(12) United States Patent
Moriyama

(10) Patent No.: US 8,784,302 B2
(45) Date of Patent: Jul. 22, 2014

(54) ENDOSCOPE

(75) Inventor: Hiroki Moriyama, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/569,299

(22) Filed: Aug. 8, 2012

(65) Prior Publication Data

US 2013/0041222 A1 Feb. 14, 2013

Related U.S. Application Data

(63) Continuation of application No. PCT/JP2011/063948, filed on Jun. 17, 2011.

(60) Provisional application No. 61/473,372, filed on Apr. 8, 2011.

(51) Int. Cl.
*A61B 1/00* (2006.01)
*A61B 1/04* (2006.01)

(52) U.S. Cl.
CPC ......... *A61B 1/00135* (2013.01); *A61B 1/00156* (2013.01); *A61B 1/00154* (2013.01); *A61B 1/00073* (2013.01); *A61B 1/00142* (2013.01); *A61B 1/0016* (2013.01)
USPC ............................ 600/114; 600/106; 600/117

(58) Field of Classification Search
CPC ........... A61B 1/00156; A61B 1/00073; A61B 1/00135; A61B 1/00142; A61B 1/00154; A61B 1/0016
USPC .......... 600/106, 110, 114, 136, 137, 121–125
See application file for complete search history.

(56) References Cited

U.S. PATENT DOCUMENTS

| 8,317,678 | B2 * | 11/2012 | Frassica et al. ............... 600/101 |
| 2005/0272976 | A1 * | 12/2005 | Tanaka et al. ................. 600/114 |
| 2006/0270901 | A1 | 11/2006 | Bern et al. |
| 2007/0167684 | A1 | 7/2007 | Toyama |
| 2010/0076264 | A1 | 3/2010 | Tallarida et al. |

FOREIGN PATENT DOCUMENTS

| EP | 2 566 564 | 3/2013 |
| JP | 55-112505 A | 8/1980 |
| JP | 1-229219 A | 9/1989 |
| JP | 2-131738 A | 5/1990 |

(Continued)

OTHER PUBLICATIONS

Japanese Office Action dated Oct. 30, 2012 from corresponding Japanese Patent Application No. 2012-531583, together with an English language translation.

(Continued)

*Primary Examiner* — Alireza Nia
(74) *Attorney, Agent, or Firm* — Scully, Scott, Murphy & Presser, P.C.

(57) ABSTRACT

An endoscope includes a drive force transmitting section attached to an insertion main body, and configured to transmit rotational drive force that rotates an attachment unit to the attachment unit, and a member inserting portion provided to a proximal direction side of an insertion section. The endoscope includes a first linear member insertable into the insertion section from the member inserting portion and removable from the insertion section through the member inserting portion, and has a distal end connectable to the drive force transmitting section while being inserted into the insertion section. The first linear member is configured to transmit the rotational drive force to the drive force transmitting section when rotated while being connected to the drive force transmitting section.

12 Claims, 17 Drawing Sheets

(56) References Cited

FOREIGN PATENT DOCUMENTS

| | | |
|---|---|---|
| JP | 10-127564 A | 5/1998 |
| JP | 2002-330924 A | 11/2002 |
| JP | 2003-325438 A | 11/2003 |
| JP | 2005-253892 A | 9/2005 |
| JP | 2005-31912 | 11/2005 |
| JP | 2005-329080 A | 12/2005 |
| JP | 2006-218231 A | 8/2006 |
| JP | 2007-29556 A | 2/2007 |
| JP | 2007-125356 A | 5/2007 |
| JP | 2007-185394 | 7/2007 |
| JP | 2007-319547 A | 12/2007 |
| JP | 2008-080119 | 4/2008 |
| JP | 2009-501555 A | 1/2009 |
| JP | 2013516296 A | 5/2013 |
| WO | WO 2005/087082 A1 | 9/2005 |
| WO | WO 2006/123590 A1 | 11/2006 |
| WO | WO 2009/143077 A1 | 11/2009 |
| WO | 2011/140118 A1 | 11/2011 |

OTHER PUBLICATIONS

Japanese Office Action dated Feb. 12, 2013 from corresponding Japanese Patent Application No. 2012-531583 together with an English language translation.
Japanese Office Action dated Feb. 12, 2013 from corresponding Japanese Patent Application No. 2012-543829 together with an English language translation.
Japanese Office Action dated Feb. 12, 2013 from corresponding Japanese Patent Application No. 2012-5543831 together with an English language translation.
Japanese Office Action dated Feb. 12, 2013 from corresponding Japanese Patent Application No. 2012-5543832 together with an English language translation.
Extended Supplementary European Search Report dated Mar. 7, 2014 from related European Application No. 11 86 3142.3.
Extended Supplementary European Search Report dated Mar. 4, 2014 from related European Application No. 11 86 2974.0.
Extended Supplementary European Search Report dated Mar. 7, 2014 from related European Application No. 11 86 3079.7.

* cited by examiner

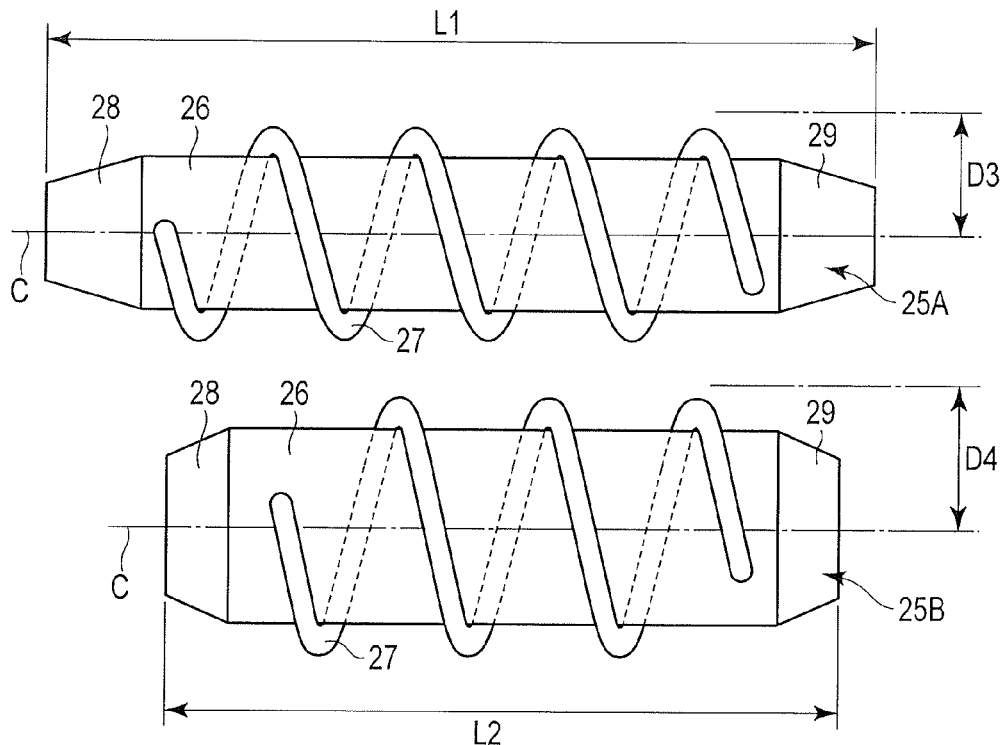
F I G. 12
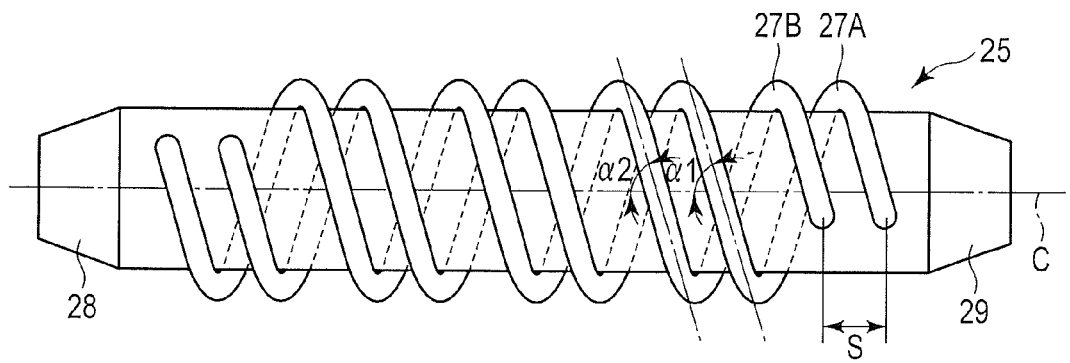
F I G. 13

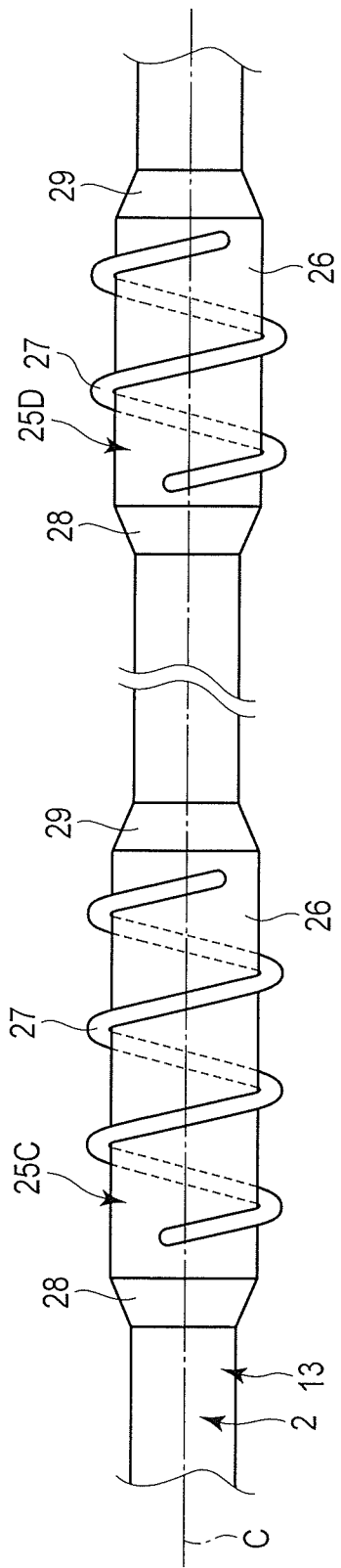
F I G. 14

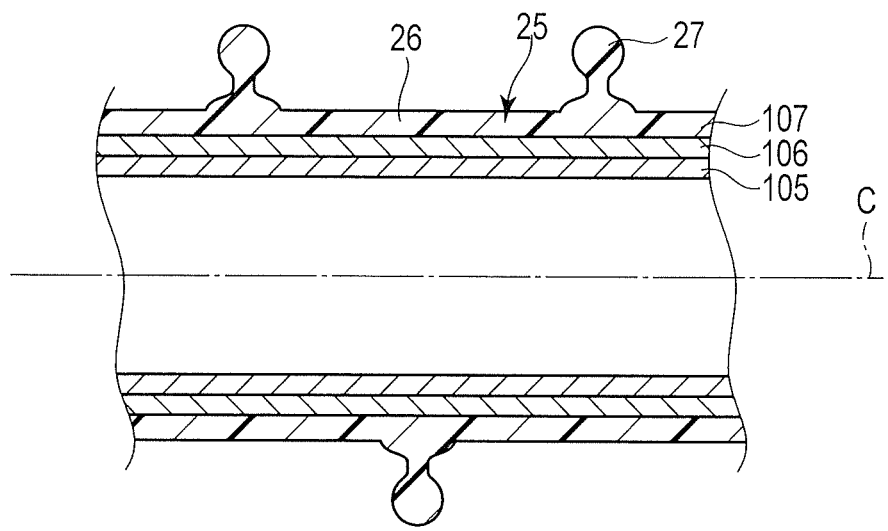
F I G. 15

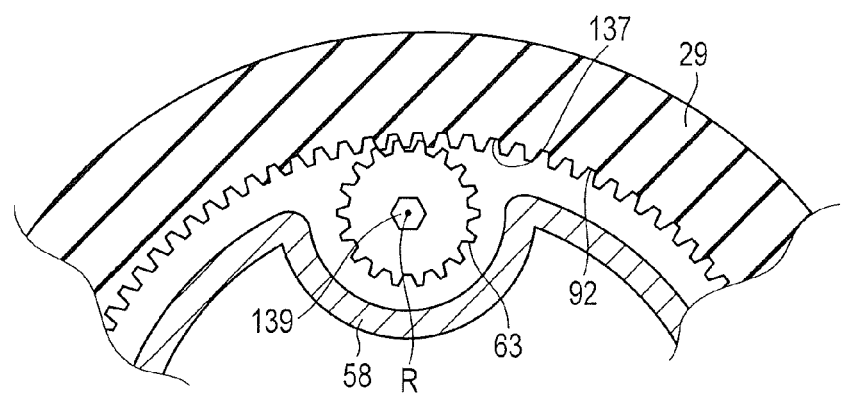
F I G. 22
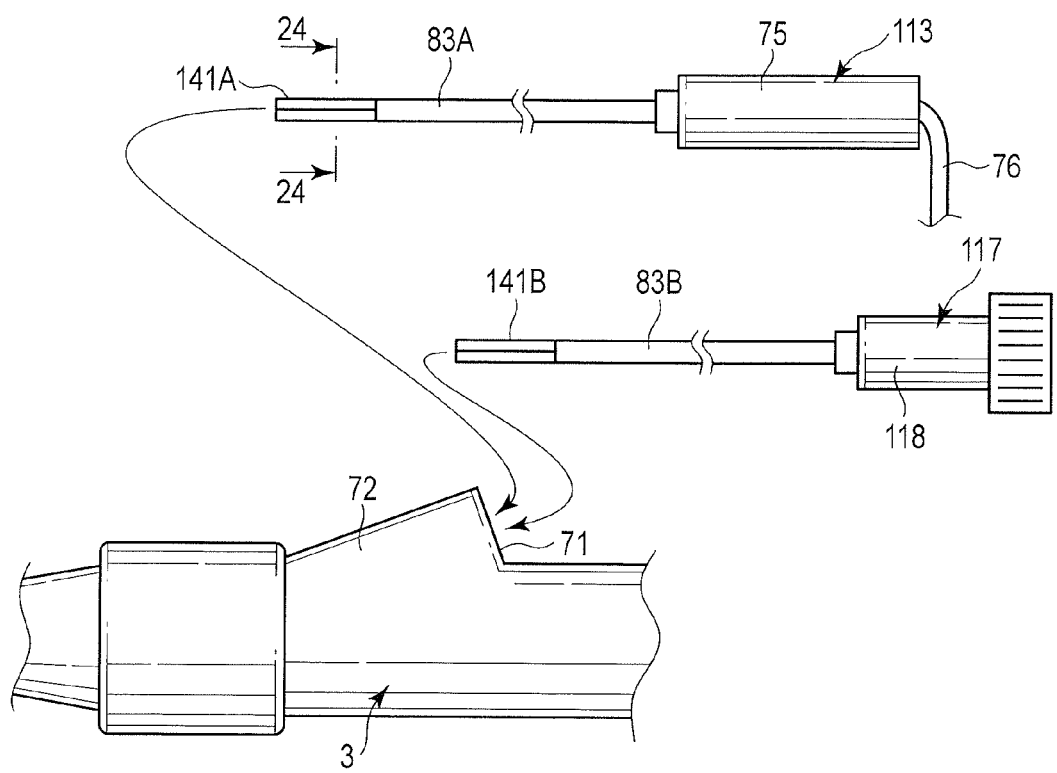
F I G. 23
F I G. 24

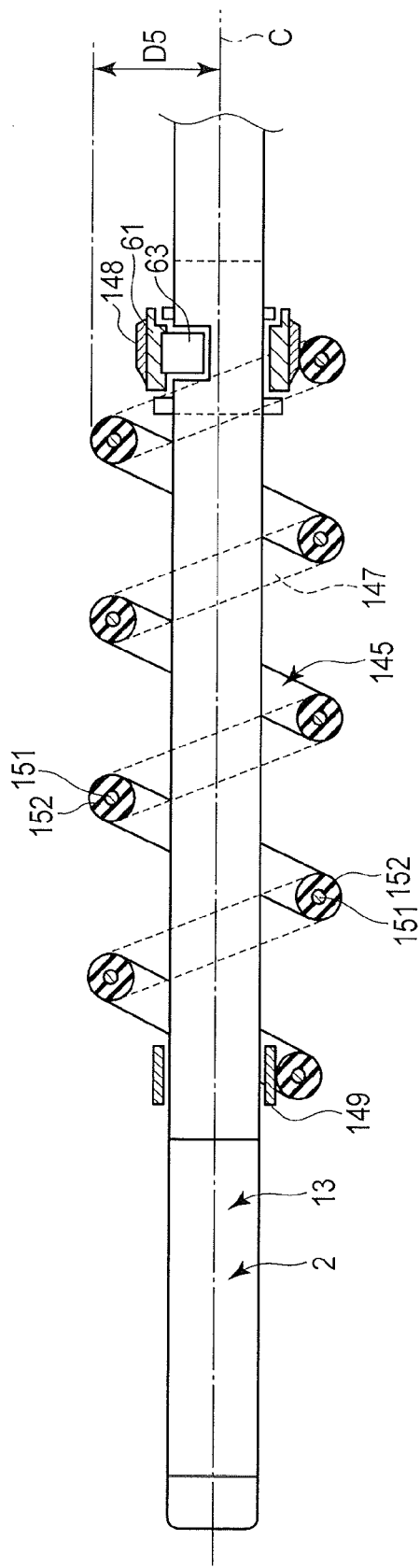
F I G. 25

ENDOSCOPE

CROSS-REFERENCE TO RELATED APPLICATIONS

This is a Continuation Application of PCT Application No. PCT/JP2011/063948, filed Jun. 17, 2011 and based upon and claiming the benefit of priority from prior U.S. Provisional Applications No. 61/473,372, filed Apr. 8, 2011, the entire contents of which are incorporated herein by reference.

BACKGROUND OF THE INVENTION

1. Field of the Invention

The present invention relates to an endoscope including an insertion section configured to be inserted into a lumen.

2. Description of the Related Art

US 2010/0076264 discloses an endoscope including an insertion section which is configured to be inserted into a lumen, and an attachment unit which is rotatable about a longitudinal axis with respect to the insertion section. The attachment unit includes a tube main body, and a fin portion spirally provided on an outer peripheral portion of the tube main body along the longitudinal axis. Further, a ring-like rotor is disposed on an outer peripheral portion of the insertion section to be rotatable about the longitudinal axis with respect to the insertion section. The attachment unit is disposed on the rotator in a fixed state. Therefore, when the rotor rotates, the attachment unit and the rotor integrally rotate about the longitudinal axis with respect to the insertion section. Furthermore, at a position where the rotor is not placed in directions parallel to the longitudinal axis, a gap is provided between the attachment unit and the outer peripheral portion of the insertion section, whereby rotation properties of the attachment unit with respect to the insertion section is improved. Therefore, at each of a distal end and a proximal end of the attachment unit, the gap is provided between the attachment unit and the outer peripheral portion of the insertion section.

When such a configuration, when the insertion section of the endoscope is inserted into a lumen, for example, the inside of a small intestine or the inside of a large intestine, the fin portion of the attachment unit comes into contact with a paries. In this state, when the rotor and the attachment unit are rotated with respect to the insertion section, propulsive force in the directions parallel to the longitudinal axis acts on the insertion section. With the propulsive force, insertability of the insertion section of the endoscope in the lumen is improved.

Further, Jpn. Pat. KOKAI Publication No. 2005-319121 discloses an endoscope in which an attachment unit rotates about a longitudinal axis together with a rotor by rotation of a rotary gear about a gear axis. In this endoscope, the rotary gear is connected to a drive member such as a motor through a flexible shaft which is a linear member. Drive force of the drive member is transmitted to the rotary gear through a flexible shaft. When the drive force of the drive member is transmitted, the rotary gear rotates about the gear axis.

BRIEF SUMMARY OF THE INVENTION

According to one aspect of the invention, an endoscope includes that an insertion section which includes an insertion main body extended along a longitudinal axis, and which is configured to be inserted into a lumen; an attachment unit which includes a fin portion spirally extended along the longitudinal axis, and which is provided to an outer peripheral direction side of the insertion section to be rotatable about the longitudinal axis with respect to the insertion main body; a drive force transmitting section which is attached to the insertion main body, and which is configured to transmit rotational drive force that rotates the attachment unit to the attachment unit; a member inserting portion provided to a proximal direction side of the insertion section; and a first linear member which is insertable into the insertion section from the member inserting portion and removable from the insertion section through the member inserting portion, and which has a distal end connectable to the drive force transmitting section while being inserted into the insertion section, the first linear member being configured to transmit the rotational drive force to the drive force transmitting section when rotated while being connected to the drive force transmitting section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 12 is a schematic view showing two types of attachment units that can be attached to an insertion section of an endoscope according to a fourth modification of the first embodiment;

FIG. 13 is a schematic view showing an attachment unit of an endoscope according to a fifth modification of the first embodiment;

FIG. 14 is a schematic view showing an insertion section and an attachment unit of an endoscope according to a sixth modification of the first embodiment;

FIG. 15 is a cross-sectional view schematically showing an attachment unit of an endoscope according to a seventh modification of the first embodiment;

FIG. 22 is a cross-sectional view taken along a line 22-22 in FIG. 21;

FIG. 23 is a schematic view showing a member insertion portion of an operation section of an endoscope according to a first modification of the third embodiment;

FIG. 24 is a cross-sectional view taken along a line 24-24 in FIG. 23;

FIG. 25 is a schematic view showing an insertion section and an attachment unit of an endoscope according to a fourth embodiment of the present invention;

DETAILED DESCRIPTION OF THE INVENTION

First Embodiment

Figure 1:
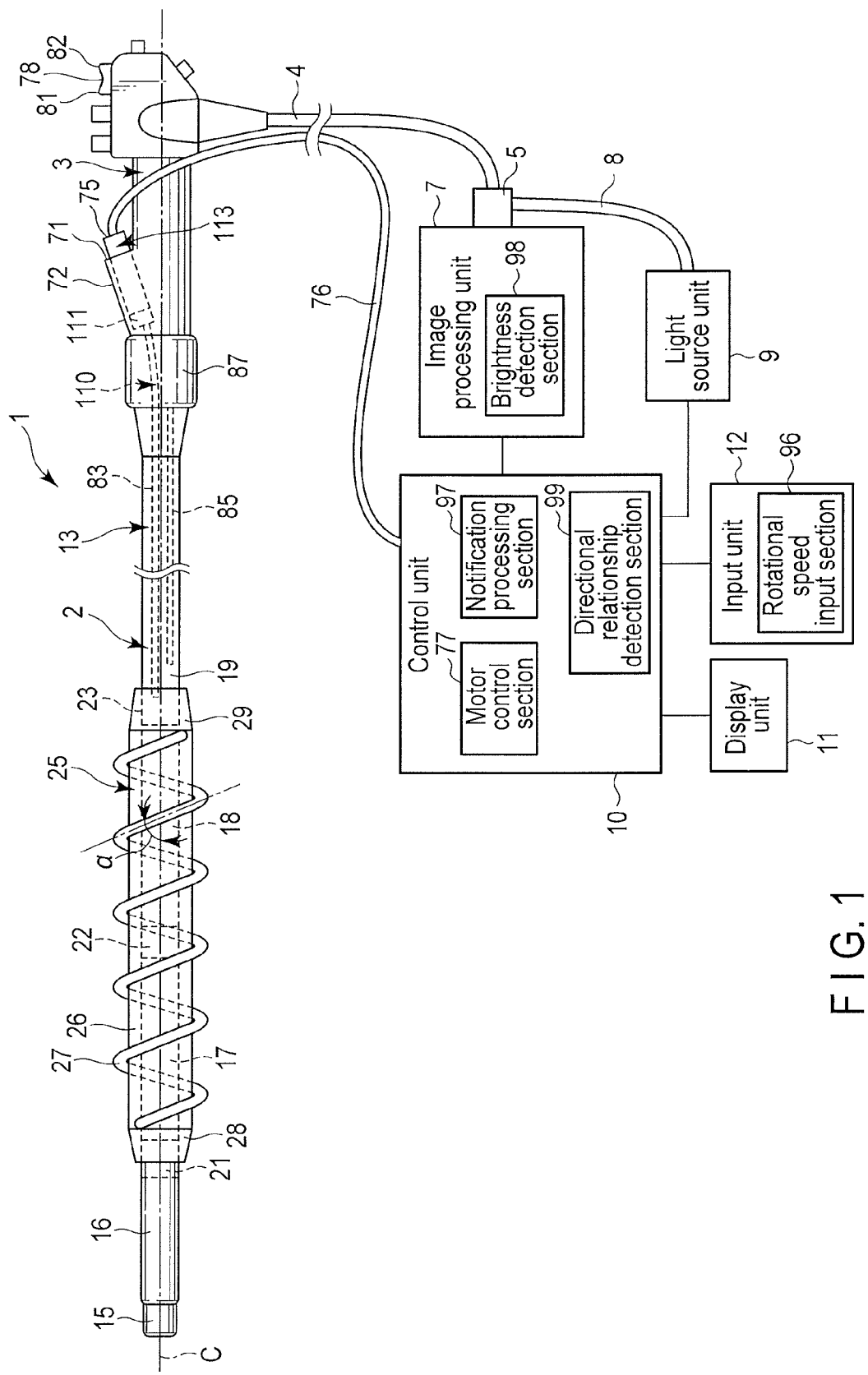
FIG. 1 is a schematic view showing an endoscope according to a first embodiment of the present invention.

A first embodiment according to the present invention will now be described with reference to FIG. 1 to FIG. 8. FIG. 1 is a view showing an endoscope 1 according to a first embodiment. As shown in FIG. 1, the endoscope 1 includes an insertion section 2, and an operation section 3 provided to a proximal direction side of the insertion section 2. The insertion section 2 is configured to be inserted into a lumen such as an inside of a small intestine or an inside of a large intestine. One end of a universal cable 4 is connected to the operation section 3. A scope connector 5 is provided at the other end of the universal cable 4. The scope connector 5 is connected to an image processing unit 7 such as an image processor. Further, one end of a light guide tube 8 is connected to the scope connector 5. Te other end of the light guide tube 8 is connected to a light source unit 9.

The image processing unit 7 and the light source unit 9 are electrically connected to a control unit 10 such as a personal computer configured to control the entire system of the endoscope 1. Furthermore, a display unit 11 such as a monitor and an input unit 12 such as a keyboard or a mouse are electrically connected to the control unit 10.

The insertion unit 2 includes an elongated insertion main body 13 which is extended along a longitudinal axis C. The insertion main body 13 includes a distal end hard portion 15 provided on the most distal direction side, an active bending portion 16 provided to a proximal direction side of the distal end hard portion 15, a passive bending portion 17 that is provided to the proximal direction side of the active bending portion 16 and configured to passively bend upon being subject to an external force, a first flexible portion 18 provided to the proximal direction side of the passive bending portion 17, and a second flexible portion 19 provided to the proximal direction side of the first flexible portion 18. The active bending portion 16 is connected to the passive bending portion 17 through a bending tube connecting portion 21. Moreover, the passive bending portion 17 is connected to the first flexible portion 18 through an intermediate connecting portion 22. Additionally, the first flexible portion 18 is connected to the second flexible portion 19 through a flexible tube connecting portion 23.

An attachment unit 25 is provided to an outer peripheral direction side of the insertion section 2. The attachment unit 25 is attached to the insertion section 2 in a state that it is rotatable about the longitudinal axis C with respect to the insertion main body 13. The attachment unit 25 includes a tube main body 26 extended along the longitudinal axis C, and a fin portion 27 spirally extended along the longitudinal axis C on an outer peripheral portion of the tube main body 26. A tube distal end portion 28 is provided in the attachment unit 25 from a distal end toward the proximal direction. Further, a tube proximal end portion 29 is provided in the attachment unit 25 from a proximal end toward the distal direction.

Figure 2:
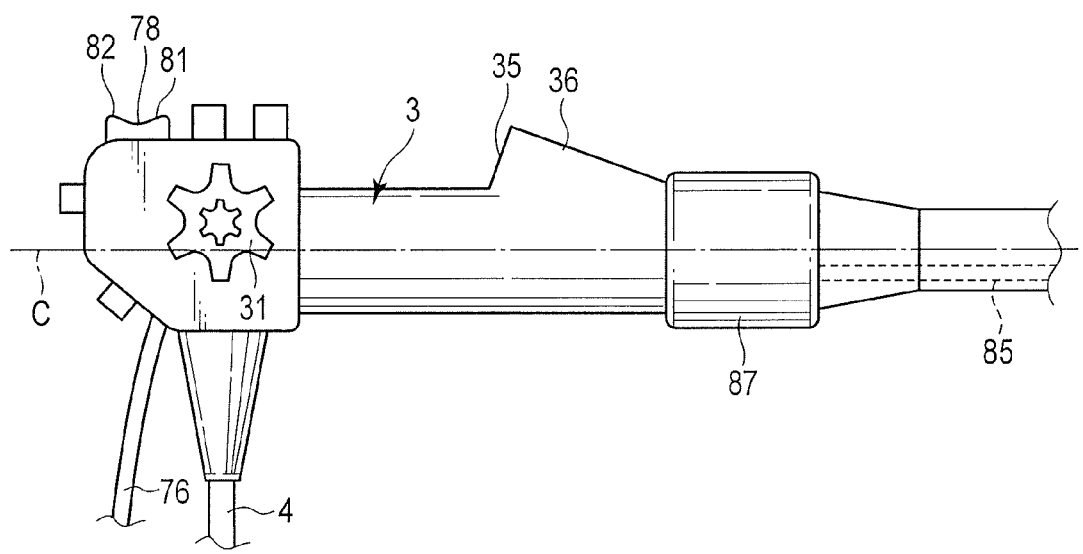
FIG. 2 is a schematic view showing a side surface of an operation section of the endoscope according to the first embodiment on the side opposite to that shown in FIG. 1.

FIG. 2 is a view showing a side surface of the operation section 3 on an opposite side of that depicted in FIG. 1. As shown in FIG. 2, a bending operation knob 31 which is a bending operation input section, to which a bending operation of the active bending portion 16 is configured to be input, is provided on an outer surface of the operation section 3. In the operation section 3, one end of a bending wire (not shown) is connected to the bending operation knob 31. The bending wire is extended in the insertion main body 13 (the insertion section 2) along the longitudinal axis C, and the other end thereof is connected to a distal end of the active bending portion 16. When the bending wire is pulled by the bending operation of the bending operation knob 31, the active bending portion 16 is bent. Further, the passive bending portion 17 is configured to passively bend when external force directly acts or when external force indirectly acts through the active bending portion 16. For example, when external force in directions perpendicular to the longitudinal axis C acts on the passive bending portion 17, the passive bending portion 17 bends. Furthermore, when external force in the directions perpendicular to the longitudinal axis C acts on the active bending portion 16, the external force also acts on the passive bending portion 17 through the active bending portion 16, and thereby the passive bending portion 17 bends.

Figure 3:
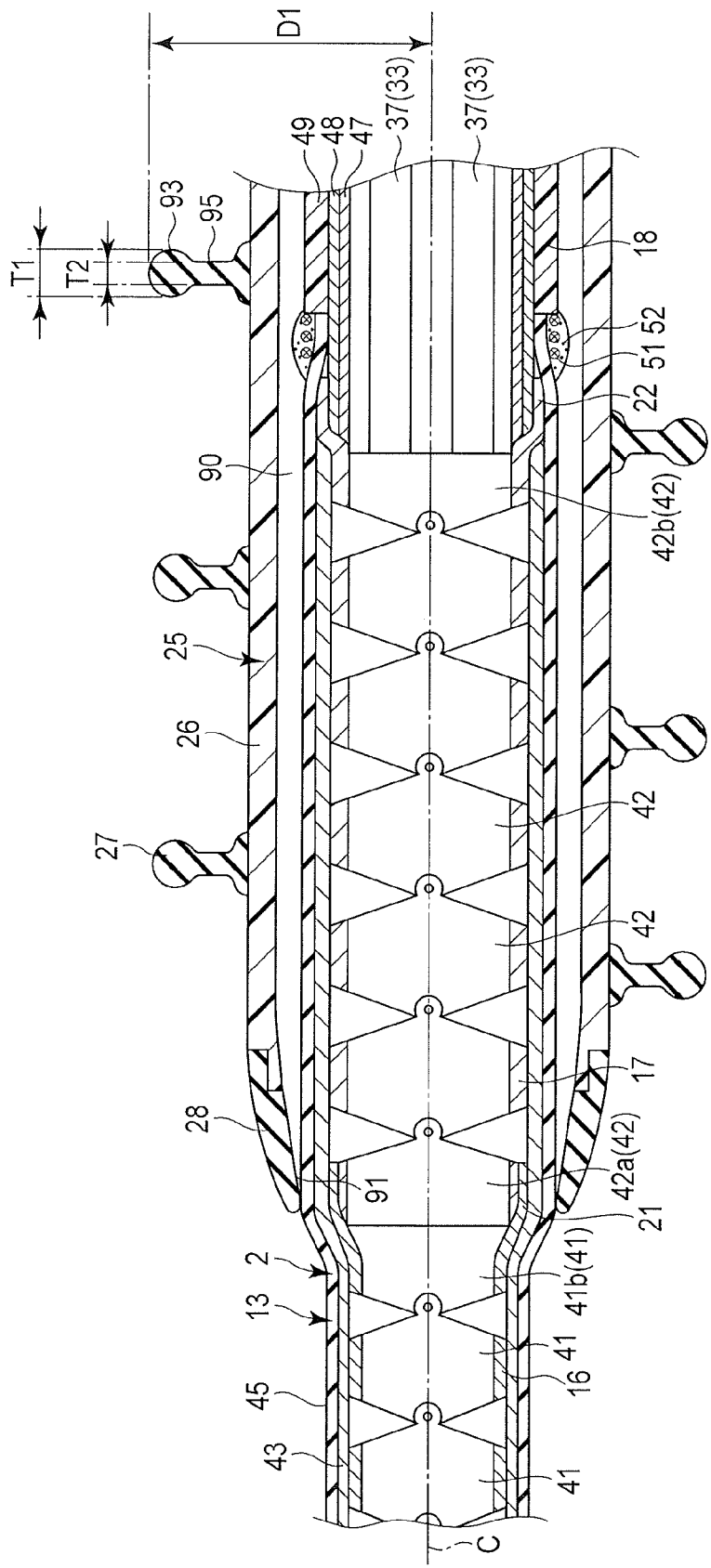
FIG. 3 is a cross-sectional view schematically showing a configuration an insertion section and an attachment unit near a passive bending portion of the endoscope according to the first embodiment.
Figure 4:
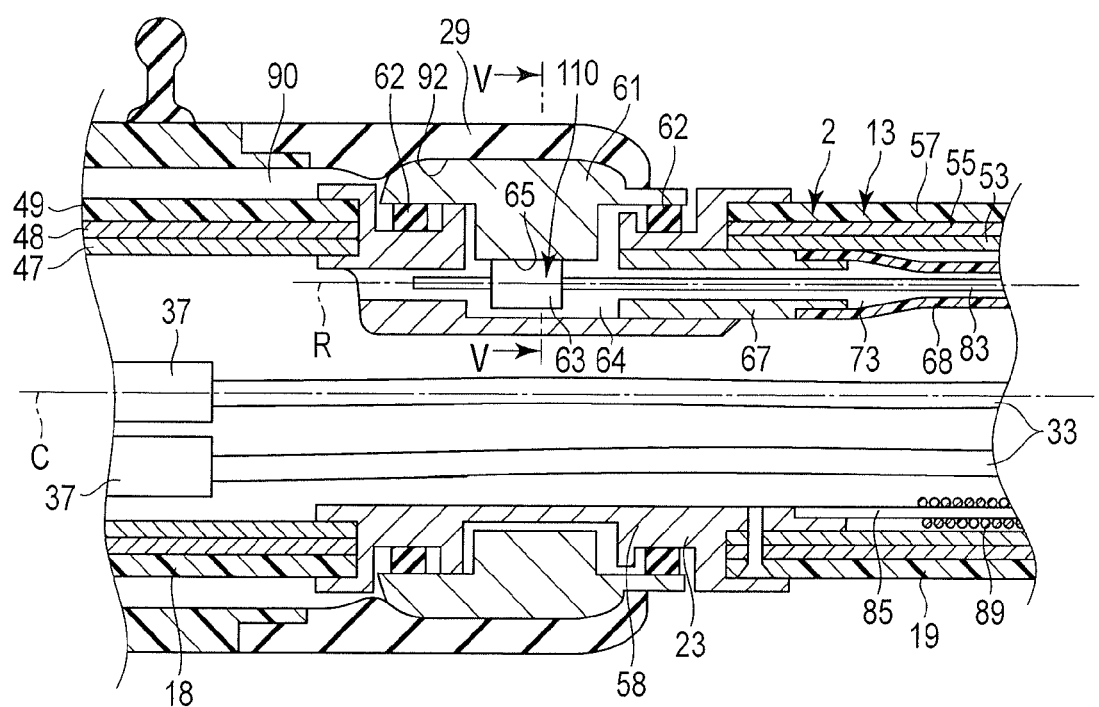
FIG. 4 is a cross-sectional view schematically showing the configuration of the insertion section and the attachment unit near a flexible tube connecting portion of the endoscope according to the first embodiment.

FIG. 3 is a view showing a configuration of the insertion section 2 and the attachment unit 25 near the passive bending portion 17. Moreover, FIG. 4 is a view showing the configuration of the insertion section 2 and the attachment unit 25 near the flexible tube connecting portion 23. As shown in FIG. 3 and FIG. 4, in the insertion main body 13 (the insertion section 2), built-in extended members 33 such as an imaging cable, a light guide tube, and others are extended along the longitudinal axis C. The built-in extended members 33 are extended from the distal end hard portion 15 provided at a distal end portion of the insertion section 2 through the inside of the insertion main body 13 (the insertion section 2) and the inside of the operation section 3.

In the distal end hard portion 15, an imaging element (not shown) configured to image a subject is provided. One end of an imaging cable which is one of the built-in extended members 33 is connected to the imaging element. The imaging cable (33) is connected to the image processing unit 7 via the scope connector 5 through the inside of the insertion main body 13 (the insertion section 2), the inside of the operation section 3, and the inside of the universal cable 4. The light guide tube which is one of the built-in extended members 33 is connected to the light guide tube 8 by the intermediary of the scope connector 5 through the inside of the insertion main body 13 (the insertion section 2), the inside of the operation section 3, and the inside of the universal cable 4. Light exiting from the light source unit 9 is led to the distal end hard portion 15 through the inside of the light guide tube 8 and the inside of the light guide tube which is the built-in extended member 33. Additionally, a subject is irradiated with the light from an illumination window (not shown) provided on the distal end hard portion 15.

As shown in FIG. 2, a treatment instrument insertion portion 36 which defines a treatment instrument insertion opening 35 into which a treatment instrument such as forceps is inserted is provided on the outer surface of the operation section 3. A treatment instrument channel tube which is one of the built-in extended members 33 is connected to the treatment instrument insertion portion 36 through the inside of the insertion main body 13 (the insertion section 2) and the inside of the operation section 3. As a result, the treatment instrument channel in the treatment instrument channel tube (33) is opened in the treatment instrument insertion opening 35. Further, the treatment instrument channel is opened in an opening portion (not shown) provided on the distal end hard portion 15. Therefore, a treatment instrument inserted from the treatment instrument insertion opening 35 protrudes from the opening portion of the distal end hard portion 15 toward the distal direction through the treatment instrument channel. Furthermore, in a state that the treatment instrument protrudes from the opening portion, a treatment using the treatment instrument is given.

As shown in FIG. 3 and FIG. 4, in a range from the active bending portion 16 to the first flexible portion 18, a protective tube 37 is provided while covering the periphery of each built-in extended member 33. A proximal end of the protective tube 37 is placed to the distal direction side of the flexible tube connecting portion 23. When the active bending portion 16 and the passive bending portion 17 (the bending portion) bend, the protective tube 37 is configured to protect each built-in extended member 33 from external force that acts on the built-in extended member 33. It is to be noted that covering the imaging cable and the light guide tube in the built-in extended members 33 with the protective tubes 37 is preferable. However, the treatment instrument channel tube has higher strength and a greater diameter than the imaging cable and the light guide tube. Therefore, it is preferable to avoid covering the treatment instrument channel tube with the protective tube 37 and to assure a space in the insertion main body 13.

As shown in FIG. 3, first bending rings 41 made of a metal are provided to the active bending portion 16. Each first bending ring 41 is coupled with an adjacent first bending ring 41 to allow its rotational movement. The distal end of the bending wire (not shown) is fixed to the first bending ring (41a) placed on the most distal direction side. When the bending wire is pulled, the first bending ring 41 rotationally moves with respect to the first bending ring 41 adjacent thereto by external force, that acts in the directions perpendicular to the longitudinal axis C, and thereby the active bending portion 16 bends.

Further, second bending rings 42 made of a metal are provided to the passive bending portion 17. Each second bending ring 42 is coupled with an adjacent second bending ring 42 to allow its rotational movement. A wire guide configured to support the bending wire is not provided to each second bending ring 42. The second bending ring 42 rotationally moves with respect to the second bending ring 42 adjacent thereto by external force, that acts in the directions perpendicular to the longitudinal axis C, and thereby the passive bending portion 17 bends.

A first bending ring 41b placed on the most proximal direction side is fixed to a second bending ring 42a placed on the most distal direction side in a fitted state. When the first bending ring 41b is fixed to the second bending ring 42a, the bending tube connecting portion 21 is formed between the active bending portion 16 and the passive bending portion 17. In the bending tube connecting portion 21, the first bending ring 41b is fixed to the second bending ring 42a, and a wall thickness of a metal portion formed of the first bending ring 41b and the second bending ring 42a is increased. Therefore, the bending tube connecting portion 21 is less flexible than the active bending portion 16 and the passive bending portion 17, and it is not bent by the external force that acts in the directions perpendicular to the longitudinal axis C.

A bending portion reticular tube (a bending portion blade) 43 made of a metal covers the outer peripheral direction side of the first bending rings 41 and the second bending rings 42. A bending portion envelope 45 covers the outer peripheral direction side of the bending portion reticular tube 43. The bending portion envelope 45 is made of, for example, fluorine-containing rubber.

With the above-described configuration, the active bending portion 16 functions as a first tubular portion, and the passive bending portion 17 functions as a second tubular portion provided to the proximal direction side of the first tubular portion. The first tubular portion (16) and the second tubular portion (17) bend when the external force acts in the directions perpendicular to the longitudinal axis C. Furthermore, the bending tube connecting portion 21 serves as a first connecting tube portion that connects the first tubular portion (16) to the second tubular portion (17). The first connecting tube portion (21) is less flexible than the first tubular portion (16) and the second tubular portion (17), and it is not bent by the external force in the directions perpendicular to the longitudinal axis C.

As FIG. 3 and FIG. 4, a first helical tube (a first flex) 47 made of a metal is provided to the first flexible portion 18. A first flexible portion reticular tube (a first flexible portion blade) 48 made of a metal covers the outer peripheral direction side of the first helical tube 47. A first flexible portion envelope 49 covers the outer peripheral direction side of the first flexible portion reticular tube 48. The first flexible portion envelope 49 is made of a material less flexible than the bending portion envelope 45, for example, a mixed resin of polyurethane and polyester. Furthermore, bending properties of the first helical tube 47, when the external force acts, are reduced as compared with that of a coupled body of the first bending rings 41 and that of a coupled body of the second bending rings 42. Therefore, the first flexible portion 18 is less flexible than the active bending portion 16 and the passive bending portion 17. However, the first flexible portion 18 is provided with flexibility that enables bending by the external force that acts in the directions perpendicular to the longitudinal axis C.

The second bending ring 42b placed on the most proximal direction side is fixed to the first helical tube 47 and the first flexible portion reticular tube 48 in a fitted state. When the second bending ring 42b is fixed to the first helical tube 47 and the first flexible portion reticular tube 48, an intermediate connecting portion 22 is formed between the passive bending portion 17 and the first flexible portion 18. In the intermediate connecting portion 22, the second bending ring 42b is fixed to the first spiral tube 47 and the first flexible portion reticular tube 48, and a wall thickness of a metal portion formed of the second bending ring 42b, the first helical tube 47, and the first flexible portion reticular tube 48 is increased. Therefore, the intermediate connecting portion 22 is less flexible than the passive bending portion 17 and the first flexible portion 18, and it is not bent by the external force that acts in the directions perpendicular to the longitudinal axis C.

Furthermore, in the intermediate connecting portion 22, a proximal end of the bending portion envelope 45 and a distal end of the first flexible portion envelope 49 are placed. A thread 51 is wound around and an adhesive 52 covers the first flexible portion envelope 49 and the bending portion envelope 45 between the bending portion envelope 45 and the first flexible portion envelope 49.

As shown in FIG. 4, the second flexible portion 19 has the same configuration as the first flexible portion 18. Therefore, a second helical tube (a second flex) 53 made of a metal is provided to the second flexible portion 19. A second flexible portion reticular tube (a second flexible portion blade) 55 covers the outer peripheral direction side of the second helical tube 53. A second flexible portion envelope 57 covers the outer peripheral direction side of the second flexible portion reticular tube 55. The second flexible portion envelope 57 is made of a material less flexible than that of the bending portion envelope 45, for example, a mixed resin of polyurethane and polyester. Moreover, the bending properties of the second helical tube 53, when the external force acts, are reduced as compared with that of the coupled body of the first bending rings 41 and that of the coupled body of the second bending rings 42. Therefore, the second flexible portion 19 is less flexible than the active bending portion 16 and the passive bending portion 17. However, the second flexible portion 19 has flexibility that enables bending by the external force that acts in the directions perpendicular to the longitudinal axis C.

A connecting mouth ring 58 made of a metal is provided to the flexible tube connecting portion 23 between the first flexible portion 18 and the second flexible portion 19. The connecting mouth ring 58 is fixed to the first helical tube 47, the first flexible portion reticular tube 48, and the first flexible portion envelope 49 in a fitted state. Additionally, the connecting mouth ring 58 is fixed to the second helical tube 53, the second flexible portion reticular tube 55, and the second flexible portion envelope 57 by fitting and with use of a fixing screw 59. A wall thickness of the connecting mouth ring 58 is greater than a wall thickness of the first helical tube 47 and a wall thickness of the second helical tube 53. Further, the connecting mouth ring 58 is less flexible than the first helical tube 47 and the second helical tube 53. Therefore, the flexible tube connecting portion 23 is less flexible than the first flexible portion 18 and the second flexible portion 19, and it is not bent by the external force that acts in the directions perpendicular to the longitudinal axis C.

With the above-described configuration, the first flexible portion 18 functions as a third tubular portion provided to the proximal direction side of the passive bending portion 17, which is the second tubular portion, and the second flexible portion 19 serves as a fourth tubular portion provided to the proximal direction side of the third tubular portion. The third tubular portion (18) and the fourth tubular portion (19) bend when the external force acts in the directions perpendicular to the longitudinal axis C. Further, the flexible tube connecting portion 23 serves as a second connecting tube portion that connects the third tubular portion (18) to the fourth tubular portion (19). The second connecting tube portion (23) is less flexible than the third tubular portion (18) and the fourth tubular portion (19), and it is not bent by the external force in the directions perpendicular to the longitudinal axis C.

As shown in FIG. 4, a rotor (a second rotor) 61 is attached to the connecting mouth ring 58 through an elastic member 62. The rotor 61 is attached to the flexible tube connecting portion 23 (the second connecting tube portion) of the insertion main body 13 in a state that it can rotate about the longitudinal axis C with respect to the insertion main body 13 integrally with the attachment unit 25. Furthermore, water-tightness is maintained between the rotor 61 and the connecting mouth ring 58 by the elastic member 62.

Moreover, a rotary gear 63 is attached to the connecting mouth ring 58. The rotary gear 63 is rotatable about a gear axis R. The rotary gear 63 is placed on an outer peripheral portion of the connecting mouth ring 58 of the insertion main body 13 and inside the rotor 61 of the insertion section 2. That is, a gear arrangement cavity 64 where the rotary gear 63 is placed is formed between the rotor 61 and the connecting mouth ring 58. Here, when the water-tightness is maintained between the rotor 61 and the connecting mouth ring 58 by the elastic member 62, inflow of a liquid into the gear arrangement cavity 64 from the outside of the insertion section 2 is avoided. Therefore, inflow of the liquid into the insertion main body 13, where the built-in extended members 33 are provided, is avoided.

Figure 5:
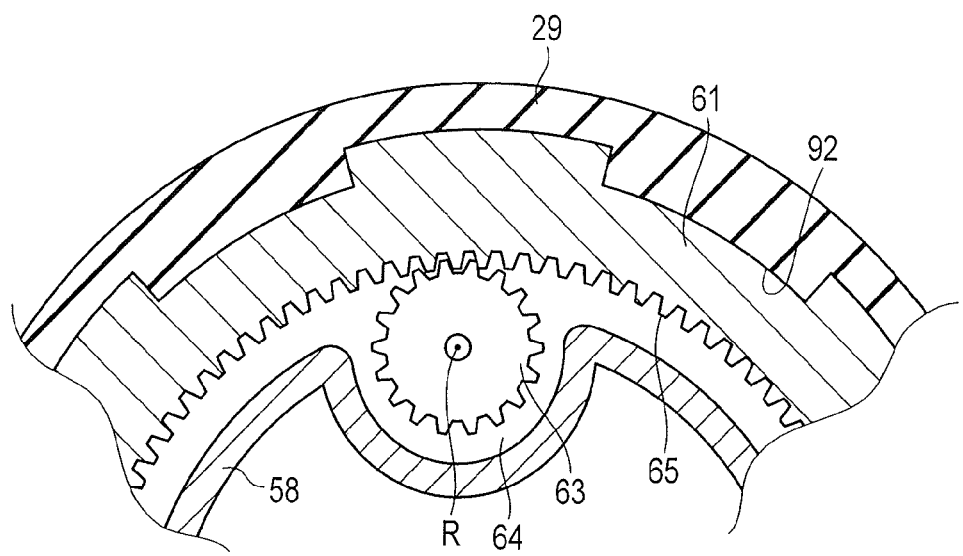
FIG. 5 is a cross-sectional view taken along a line V-V in FIG. 4.

FIG. 5 is a cross-sectional view taken along a line V-V in FIG. 4. As shown in FIG. 5, a gear portion 65 configured to mesh with the rotary gear 63 is provided on an inner peripheral portion of the rotor 61. As a result, the rotor 61 rotates about the longitudinal axis C in accordance with rotation of the rotary gear 63 about the gear axis R. Moreover, the rotary gear 63 and the gear portion 65 of the rotor 61 are separated from the built-in extended members 33 in the insertion main body 13 by the connecting mouth ring 58. That is, the connecting mouth ring 58 functions as a partition member configured to separate the rotary gear 63 and the gear portion 65 of the rotor 61 from the built-in extended members 33. As a result, the rotary gear 63 and the gear portion 65 are prevented from coming into contact with the built-in extended members 33.

Additionally, the proximal end of the protective tube 37, that covers each built-in extended member 33, is placed to the distal direction side of the flexible tube connecting portion 23, to which the rotary gear 63 is disposed. That is, the proximal end of the protective tube 37 is placed to the distal direction side of the rotary gear 63. The rotary gear 63, the rotor 61, and others as members, those are configured to rotate the attachment unit 25, are disposed to the flexible tube connecting portion 23. Therefore, an inner diameter of the flexible tube connecting portion 23 (the connecting mouth ring 58) is smaller than an inner diameter of the passive bending portion 17, an inner diameter of the first flexible portion 18, and others. Therefore, when the proximal end of the protective tube 37, that covers each built-in extended member 33, is placed to the distal direction side of the flexible tube connecting portion 23, a space in the flexible tube connecting portion 23 is assured. It is to be noted that the first flexible portion 18 and the second flexible portion 19 (the flexible portions) are less flexible than the active bending portion 16 and the passive bending portion 17 (bending portions). Therefore, the external force that acts on the built-in extended members 33 when bent is smaller in the flexible portions (18, 19) than in the bending portions (16, 17). Therefore, in the flexible portions (18, 19), the built-in extended members 33 do not have to be covered with the protective tubes 37.

As shown in FIG. 4, a metal connection pipe 67 is attached to the connecting mouth ring 58. A channel tube 68 is connected to the connection pipe 67. The channel tube 68 is extended to the proximal direction in the insertion main body 13 (the insertion section 2) along the longitudinal axis C. It is to be noted that the channel tube 68 is a channel tube (68) different from the treatment instrument channel tube, which is one of the built-in extended members 33.

As shown in FIG. 1, a member insertion portion (an attachment portion) 72 that defines a member insertion opening 71 is provided on the outer surface of the operation section 3. The channel tube 68 is connected to the member insertion portion 72 through the inside of the insertion main body 13 (the insertion section 2) and the inside of the operation section 3. As a result, a channel 73 in the channel tube 68 is opened in the member insertion opening 71. Further, as shown in FIG. 4, the channel 73 is extended to the gear arrangement cavity 64 from the inside of the channel tube 68 through the inside of the connection pipe 67. As described above, the channel 73 is extended from the member insertion opening 71 on the outer surface of the operation section 3 to the gear arrangement cavity 64 through the inside of the operation section 3 and the inside of the insertion section 2. That is, the member insertion portion 72, the channel tube 68, and the connection pipe 67 constitute a channel defining portion that defines the channel 73.

As shown in FIG. 1, a motor 75 as a drive member inserted from the member insertion opening 71 is attached to the member insertion portion 72. That is, the member insertion member 72 serves as an attachment portion to which the motor 75 is attached to. One end of a motor cable 76 is connected to the motor 75. The other end of the motor cable 76 is connected to the control unit 10. The control unit 10 includes a motor control section 77 configured to control rotational drive of the motor 75. Furthermore, a rotating operation input switch 78 as a rotating operation input section that is configured to input a rotating operation of the motor 75 is provided on the outer surface of the operation section 3. The rotating operation input switch 78 is electrically connected to the motor control section 77 through an electrical signal line or the like in the universal cable 4. Moreover, the rotating operation input switch 78 includes a first pressing portion 81, and a second pressing portion 82 placed to the proximal direction side of the first pressing portion 81.

Additionally, as shown in FIG. 1 and FIG. 4, the motor 75 is connected to the rotary gear 63 by a linear member 83 such as a wire. The linear member 83 is extended along the channel 73. Based on the rotational drive of the motor 75, the linear member 83 rotates about the gear axis R, and thereby the rotary gear 63 rotates.

With the above-described configuration, when the first pressing portion 81 of the rotating operation input switch 78 is pressed, the motor 75 is rotated and driven in a counterclockwise direction as seen from the proximal direction by the motor control section 77. As a result, the linear member 83 and the rotary gear 63 rotate in the counterclockwise direction as seen from the proximal direction. When the rotary gear 63 rotates in the counterclockwise direction, the rotor 61 rotates about the longitudinal axis C in a clockwise direction as seen from the proximal direction. On the other hand, when the first pressing portion 81 of the rotating operation input switch 78 is pressed, the motor 75 is rotated and driven in the clockwise direction as seen from the proximal direction by the motor control portion 77. As a result, the linear member 83 and the rotary gear 63 rotate in the clockwise direction as seen from the proximal direction. When the rotary gear 63 rotates in the clockwise direction, the rotor 61 rotates about the longitudinal axis C in the counterclockwise direction as seen from the proximal direction.

As shown in FIG. 4, a pulling wire 85 is fixed to the connecting mouth ring 58 of the flexible connecting portion 23. Additionally, as shown in FIG. 1, a flexibility adjustment knob 87 as a flexibility adjustment section that is configured to change the flexibility of the second flexible portion 19 is provided on the outer surface of the operation section 3. The proximal end of the pulling wire 85 is connected to the flexibility adjustment knob 87 in the operation section 3. When the flexibility adjustment knob is operated, the pulling wire 85 is pulled in the proximal direction.

Additionally, as shown in FIG. 4, a coil pipe 89 through which the pulling wire 85 is inserted is provided in the second flexible portion 19. A distal end of the coil pipe 89 is fixed to the pulling wire 85 by brazing and the like. Further, the distal end of the coil pipe 89 is placed to the proximal direction side of a proximal end of the attachment unit 25. A proximal end of the coil pipe 89 is fixed to an inner peripheral portion of the operation section 3 to the proximal direction side of a proximal end of the second flexible portion 19. When the pulling wire 85 is pulled, compression force in directions parallel to the longitudinal axis C acts on the coil pipe 89. When the compression force acts, hardness of the coil pipe 89 is increased, and the flexibility of the second flexible portion 19 is reduced.

As shown in FIG. 1 and FIG. 3, the tube distal end portion 28 of the attachment unit 25 is placed to the outer peripheral direction side of the bending tube connecting portion 21, which is the first connecting tube portion. Furthermore, as shown in FIG. 1 and FIG. 4, the tube proximal end portion 29 of the attachment unit 25 is placed to the outer peripheral direction side of the flexible tube connecting portion 23, which is the second connecting tube portion. Moreover, the tube main body 26 is extended along the longitudinal axis C between the tube distal end portion 28 and the tube proximal end portion 29. With the above-described configuration, the attachment unit 25 is extended along the longitudinal axis C from the position to the outer peripheral direction side of the bending tube connecting portion 21 to the position to the outer peripheral direction side of the flexible tube connecting portion 23. That is, a part of the attachment unit 25 is placed to the outer peripheral direction side of the passive bending portion 17.

The tube main body 26 is made of a resin such as polyurethane. The tube main body 26 has a gap 90 between itself and the bending portion envelope 45 or the first flexible portion envelope 49. That is, the tube main body 26 is provided in a state that it has the gap 90 between itself and the outer peripheral portion of the insertion section 2 or the member disposed on the outer peripheral portion of the insertion section 2 (for example, the adhesive 52).

The tube distal end portion 28 is made of a material such as rubber softer than the tube main body 26. Therefore, as shown in FIG. 3, a distal side gap reduction portion 91, which is configured to eliminate the gap 90 or reduce the gap 90 to be smaller than that in a part to the inner peripheral direction side of the tube main body 26, is formed on an inner peripheral portion of the tube distal end portion 28 between the attachment unit 25 and the bending portion envelope 45. The gap 90 is eliminated or the gap 90 is reduced to be smaller than that in a part to the inner peripheral direction side of the tube main body 26 between the attachment unit 25 and the outer peripheral portion of the insertion section 2 or the member disposed on the outer peripheral portion of the insertion section 2 by the distal side gap reduction portion 91.

The tube proximal end portion 29 is made of a material such as rubber softer than the tube main body 26. Therefore, as shown in FIG. 4 and FIG. 5, a proximal side gap reduction portion 92, which is configured to eliminate the gap 90 or reduce the gap 90 to be smaller than that in the part on the inner peripheral direction side of the tube main body 26, is provided on an inner peripheral portion of the tube proximal end portion 29 between the attachment unit 25 and the connecting mouth ring 58 or the rotor 61. The gap 90 is eliminated or the gap 90 is reduced to be smaller than that in the part on the inner peripheral direction side of the tube main body 26 between the attachment unit 25 and the outer peripheral portion of the insertion section 2 or the member disposed on the outer peripheral portion of the insertion section 2 by the proximal side gap reduction portion 92. Moreover, the tube proximal end portion 29 is fixed to the rotor (the second rotor) 61 of the insertion section 2 without the gap 90 by the proximal side gap reduction portion 92. Therefore, when the rotor 61 rotates, the attachment unit 25 rotates about the longitudinal axis C with respect to the insertion main body 13 integrally with the rotor 61.

The fin portion 27 extended on the outer peripheral portion of the tube main body 26 is made of rubber or the like. The fin portion 27 is fixed to the tube main body 26 by adhesion or welding. As shown in FIG. 1, the fin portion 27 is extended in the spiral form in the clockwise direction as seen from the proximal direction. Additionally, the fin portion 27 is extended in a state that an acute angle α with respect to the longitudinal axis C becomes greater than 45°. When the insertion section 2 of the endoscope 1 is inserted into the lumen such as an inside of a small intestine or an inside of a large intestine, the fin portion 27 of the attachment unit 25 comes into contact with a paries. In this state, the rotor 61 and the attachment unit 25 are rotated about the longitudinal axis C with respect to the insertion main body 13. As a result, propulsive force in one of the directions parallel to the longitudinal axis C acts on the insertion section 2.

In this embodiment, the fin portion 27 is extended in the spiral form in the clockwise direction as seen from the proximal direction. Therefore, when the rotor 61 and the attachment unit 25 rotate in the clockwise direction as seen from the proximal direction, the propulsive force toward the distal direction acts on the insertion section 2. As a result, insertability of the insertion section 2 in the lumen can be improved. On the other hand, when the rotor 61 and the attachment unit 25 rotate in the counterclockwise direction as seen from the proximal direction, the propulsive force toward the proximal direction acts on the insertion section 2. As a result, removability of the insertion section 2 in the lumen can be improved.

It is to be noted that, in this embodiment, when the first pressing portion 81 of the rotating operation input switch 78 is pressed, the rotor 61 rotates in the clockwise direction. Furthermore, when the second pressing portion 82 is pressed, the rotor 61 rotates in the counterclockwise direction. That is, the propulsive force toward the distal direction is exerted when the first pressing portion 81 is pressed, and the propulsive force toward the proximal direction is exerted when the second pressing portion 82 placed to the proximal direction side of the first pressing portion 81 is pressed. Therefore, an operator can readily perform operations by using the rotating operation input switch 78.

Additionally, the fin portion 27 may be extended in the spiral shape in the counterclockwise direction as seen from the proximal direction. In this case, when the rotor 61 and the attachment unit 25 rotate in the clockwise direction as seen from the proximal direction, the propulsive force toward the proximal direction acts on the insertion section 2. On the other hand, when the rotor 61 and the attachment unit 25 rotate in the counterclockwise direction as seen from the proximal direction, the propulsive force toward the distal direction acts on the insertion section 2. However, when the insertion section 2 is inserted into the large intestine, it is preferable for the fin portion 27 to be spirally formed in the clockwise direction as seen from the proximal direction in terms of a relationship with a shape of the large intestine and others, like this embodiment.

As shown in FIG. 3 and FIG. 4, the fin portion 27 includes a first width dimension portion 93 to which the outer peripheral end is placed in a state that the external force is not exerted in the directions parallel to the longitudinal axis C. In the state that the external force is not exerted in the directions parallel to the longitudinal axis C, the first width dimension portion 93 has a first width dimension T1 in the directions parallel to the longitudinal axis C. Further, a second width dimension portion 95 is provided to the inner peripheral direction side of the first width dimension portion 93. In the state that the external force is not exerted in the directions parallel to the longitudinal axis C, the second width dimension portion 95 has a second width dimension T2 smaller than the first width dimension T1 in the directions parallel to the longitudinal axis C. In the state that the external force is not exerted in the directions parallel to the longitudinal axis C, the outer peripheral end of the fin portion 27 placed at the first width dimension portion 93 comes into contact with the paries. Furthermore, in the state that the external force is not exerted in the directions parallel to the longitudinal axis C, a dimension from the longitudinal axis C to the outer peripheral end of the fin portion 27 is D1.

Figure 6:
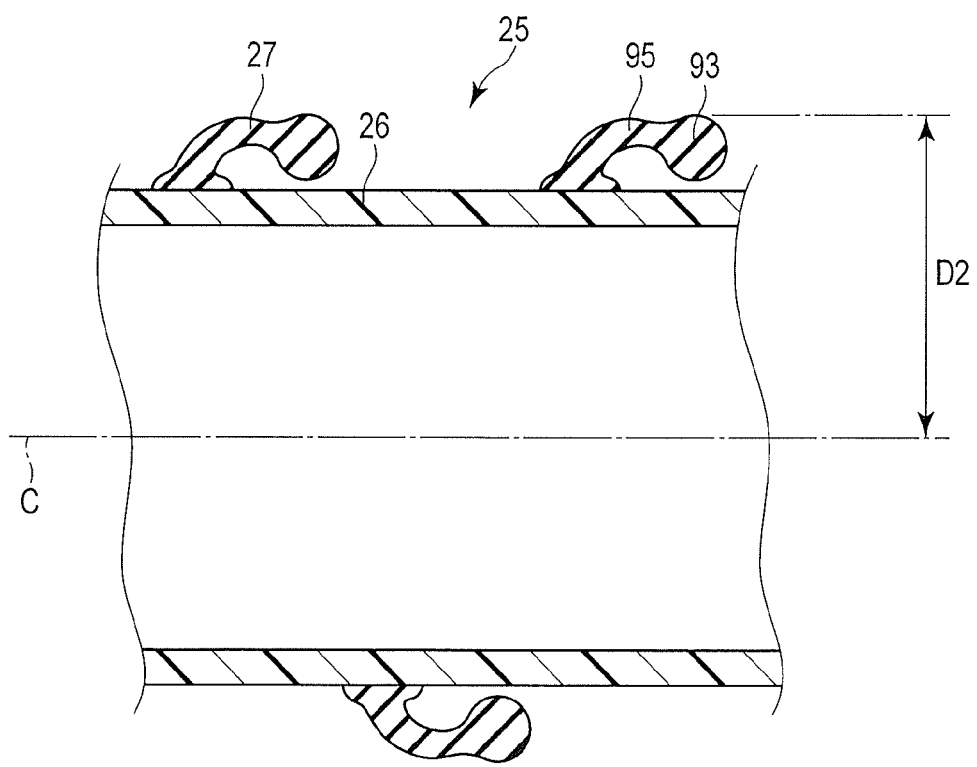
FIG. 6 is a cross-sectional view schematically showing a state that external force in one of directions parallel to a longitudinal axis acts on a fin portion of the attachment unit according to the first embodiment.

FIG. 6 is a view showing a state that the external force in one of the directions parallel to the longitudinal axis C acts on the fin portion 27. As shown in FIG. 6, when the external force is exerted in one of the directions parallel to the longitudinal axis C, the second width dimension portion 95 bends. As a result, the dimension from the longitudinal axis C to the outer peripheral end of the fin portion 27 is D2, and it is smaller than dimension D1 in the state that the external force is not exerted in the directions parallel to the longitudinal axis C. That is, the dimension from the longitudinal axis C to the outer peripheral end of the fin portion 27 (D1 or D2) varies in accordance with the state of exertion of the external force in the directions parallel to the longitudinal axis C. Here, dimension D1 is preferably greater than 10 mm, and dimension D2 is preferably equal to or smaller than 10 mm.

It is to be noted that, when the attachment unit 25 is rotated in the state that fin portion 27 is in contact with the paries, the external force around the longitudinal axis C acts on the fin portion 27. However, as described above, in this embodiment, the fin portion 27 is extended in a state that the acute angle α with respect to the longitudinal axis C becomes greater than 45°. Therefore, the second width dimension portion 95 hardly bends with respect to the external force around the longitudinal axis C. Moreover, since the acute angle α of the fin portion 27 with respect to the longitudinal axis C is greater than 45°, the second width dimension portion 95 is apt to bend with respect to the external force in the directions parallel to the longitudinal axis C. Therefore, the second width dimension portion 95 bends, even if the external force in one of the directions parallel to the longitudinal axis C that acts on the fin portion 27 is small external force that is not greater than 10 N.

Additionally, in a cross section parallel to the longitudinal axis C, the first width dimension portion 93 is formed into a substantially circular shape, but the present invention is not restricted thereto. For example, in the cross section parallel to the longitudinal axis C, the first width dimension portion 93 may be formed into a substantially square shape. That is, in the state that the external force is not exerted in the directions parallel to the longitudinal axis C, it is satisfactory for the second width dimension T2 of the second width dimension portion 95 to be smaller than the first width dimension T1 of the first width dimension portion 93.

Further, as shown in FIG. 1, the input unit 12 includes a rotational speed input section 96 configured to input a rotational speed of the attachment unit 25. The motor control section 77 is configured to control a rotational speed of the motor 75 based on an input in the rotational speed input section 96, and thereby configured to control the rotational speed of the attachment unit 25. Furthermore, the control unit 10 includes a notification processing section 97 configured to process notifying an operator of a state that the attachment unit 25 is rotated. Based on the processing in the notification processing section 97, the operator can recognize the state that the attachment unit 25 is rotated by display in the display unit 11, generation of sound, and others.

Moreover, the image processing unit 7 includes brightness detection section 98 configured to detect brightness of an image of a subject. The control unit 10 includes a directional relationship detection section 99 configured to detect a relationship between an insertion direction of the insertion section 2 and an extending direction of the lumen based on a detection result in the brightness detection section 98. The motor control section 77 is configured to control rotational drive of the motor 75 based on a detection result in the directional relationship detection section 99. In an image of the subject, a lumen part is dark, and a paries part is bright. Therefore, when the insertion direction of the insertion section 2 substantially coincides with the extending direction of the lumen, a central part of the image of the subject is dark. In this situation, the directional relationship detection section 99 determines that the insertion direction of the insertion section 2 substantially coincides with the extending direction of the lumen, and the motor 75 is rotated and driven by the motor control section 77. As a result, the attachment unit 25 rotates. On the other hand, when the insertion direction of the insertion section 2 is greatly different from the extending direction of the lumen in, for example, a state that the distal end of the insertion section 2 faces the paries, the central part of the image of the subject is bright. In this situation, the directional relationship detection section 99 determines that the insertion direction of the insertion section 2 is greatly different from the extending direction of the lumen, and the motor 75 is not rotated and driven by the motor control section 77. Therefore, the attachment unit 25 does not rotate.

Figure 7:
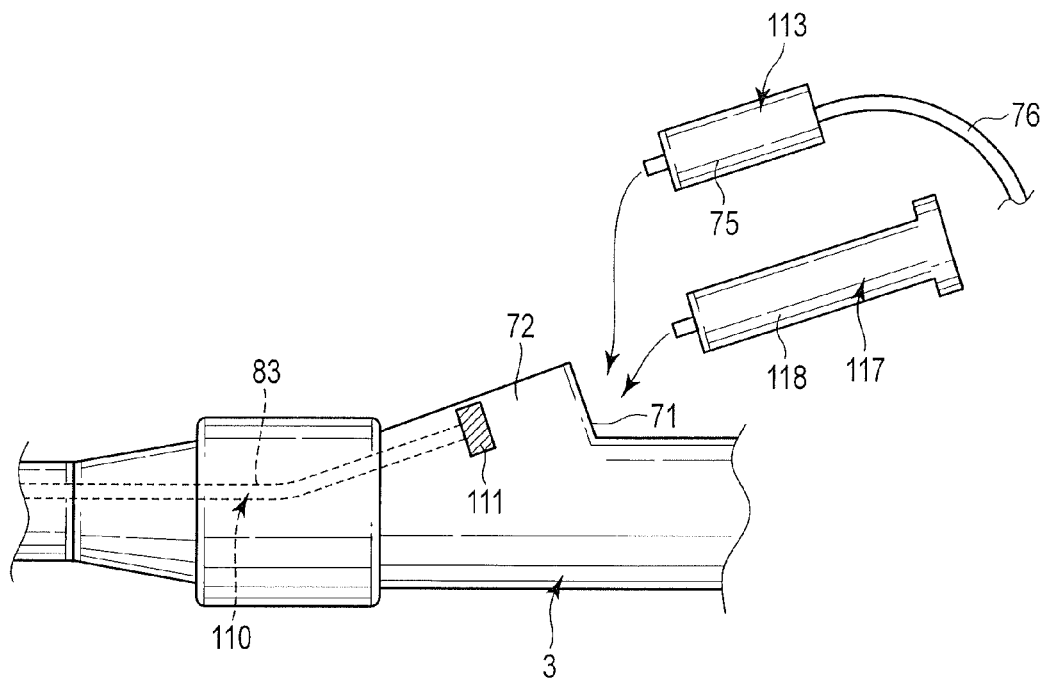
FIG. 7 is a schematic view showing a member insertion portion in an operation section of an endoscope according to the first embodiment.

FIG. 7 is a view showing a member inserting portion 72. As shown in FIG. 7, the linear member 83 is extended from the rotary gear 63 along the channel 73. A switching connecting portion 111 is provided at an end portion of the linear member 83 on the opposite side of the rotary gear 63. Here, the rotary gear 63, the linear member 83, and the switching connecting portion 111 constitute a gear unit 110.

Further, a drive unit 113 including a motor 75 or a manual rotation unit 117 including a manual rotation member 118 configured to perform manually rotational operation is selectively attached to a member inserting portion 72 as the attachment portion. In a state that the drive unit 113 is attached to the member inserting portion 72, the switching connecting portion 111 connects the linear member 83 to the motor 75. Furthermore, in a state that the manual rotation unit 117 is attached to the member inserting portion 72, the switching connecting portion 111 connects the linear member 83 to the manual rotation member 118. That is, the switching connecting portion 111 selectively connects the linear member 83 to the motor 75 as the drive member or the manual rotation member 118. As a result, the drive unit 113 or the manual rotation unit 117 is selectively connected to the gear unit 110.

In a state that the drive unit 113 is connected to the gear unit 110, the linear member 83 and the rotation gear 63 rotate about the gear axis R by the rotational drive of the motor 75. When the rotary gear 63 rotates, the rotor 61 and the attachment unit 25 rotate about the longitudinal axis C with respect to the insertion main body 13. Moreover, in a state that the manual rotation unit 117 is connected to the gear unit 110, the linear member 83 and the rotary gear 63 rotate about the gear axis R by the rotational operation of the manual rotation member 118. As a result, the rotor 61 and the attachment unit 25 rotate about the longitudinal axis C with respect to the insertion main body 13.

Figure 8:
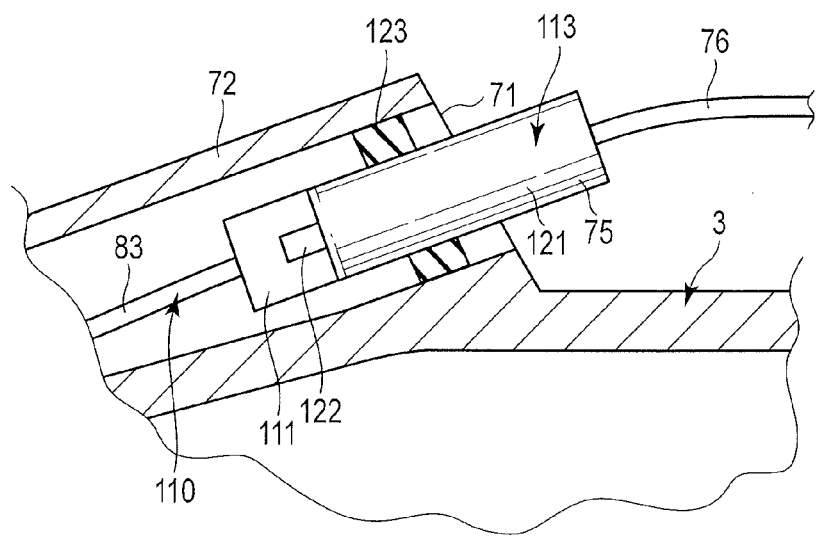
FIG. 8 is a cross-sectional view schematically showing a state that a motor is attached to the member insertion portion in the operation section of the endoscope according to the first embodiment.

FIG. 8 is a view showing a state that the motor 75 is attached to the member inserting portion 72. As shown in FIG. 8, the motor 75 includes a motor main body 21 provided in a fixed state with respect to the member inserting portion 72, and a rotary shaft portion 122 which is configured to rotate with respect to the motor main body 121 in a state that the motor 75 is driven to rotate. In a state that the drive unit 113 is connected to the gear unit 110, the linear member 83 is connected to the rotary shaft portion 122 through the switching connecting portion 111. Additionally, an elastic member 123 is provided between the member inserting portion 72 of the operation section 3 and the motor main body 121 of the motor 75. The elastic member 123 is configured to maintain water-tightness between the member inserting portion 72 and the motor 75. As a result, inflow of a liquid into the operation section 3 from the outside is avoided.

Further, in a state that the manual rotation member 118 is attached to the member inserting portion 72, the elastic member 123 is configured to maintain water-tightness between the member inserting portion 72 and the manual rotation member 118. As a result, inflow of a liquid into the operation section 3 from the outside is avoided. With the above-described configuration, the motor 75 or the manual rotation member 118 can be cleaned and sterilized while being attached to the member inserting portion 72.

A function of the endoscope 1 according to this embodiment will now be described. The insertion section 2 of the endoscope 1 is inserted into the lumen from the mouth or the anus, and it is removed from the lumen through the mouth or the anus. When inserting the insertion section 2 into the small intestine or the large intestine, and when the removing the insertion section 2 from the small intestine or the large intestine, the insertion section 2 passes through the esophagus or the anus having an inner diameter of 20 mm or below. On the other hand, each of the small intestine and the large intestine has an inner diameter greater than 20 mm.

Like the endoscope according to this embodiment, as endoscopes each including an attachment unit which is provided with a tube main body and a fin portion, there is endoscope disclosed in US2010/0076264. In this endoscope, a dimension from a longitudinal axis to an outer peripheral end of a fin portion does not change in response to a change in the state of exertion of the external force in the directions parallel to the longitudinal axis. Therefore, when the dimension from the longitudinal axis to the outer peripheral end of the fin portion is greater than 10 mm, the insertion section has a difficulty in passing through the lumen with a small inner diameter, for example, the esophagus or the anus. On the other hand, when the dimension from the longitudinal axis to the outer peripheral end of the fin portion is not greater than 10 mm, the fin portion does not come into contact with the paries in the lumen with a large inner diameter, for example, the small intestine or the large intestine. Therefore, even when the attachment unit is rotated, the propulsive force is not generated in one of the directions parallel to the longitudinal axis.

On the other hand, in the endoscope 1 according to this embodiment, the dimension (D1 or D2) from the longitudinal axis C to the outer peripheral end of the fin portion 27 changes in response to the state of exertion of the external force in the directions parallel to the longitudinal axis C. When inserting or removing the insertion section 2 into or from the lumen in the state that the attachment unit 25 is not rotated, force of 2N to 20N is applied in one of the directions parallel to the longitudinal axis C by an operator. Therefore, when the insertion section 2 passes through the lumen having a small inner diameter, the external force of 2N to 20N in one of the directions parallel to the longitudinal axis C is exerted with respect to the fin portion 27 from the paries. The second width dimension portion 95 of the fin portion 27 bends by the external force from the paries. As a result, the dimension from the longitudinal axis C to the outer peripheral end of the fin portion 27 becomes dimension D2 that is not greater than 10 mm. Therefore, the insertion section 2 can readily pass through the lumen having a small inner diameter.

Furthermore, when the insertion section 2 passes through the lumen having a large inner diameter, the external force in the directions parallel to the longitudinal axis C is not exerted from the paries with respect to the fin portion 27. Therefore, the second width dimension portion 95 of the fin portion 27 does not bend, and the dimension from the longitudinal axis C to the outer peripheral end of the fin portion 27 becomes dimension D1 greater than 10 mm. At this time, the first width dimension portion 93 of the fin portion 27 comes into contact with the paries. When the attachment unit 25 is rotated in this state, the propulsive force in one of the directions parallel to the longitudinal axis C is exerted with respect to the insertion section 2. With the propulsive force, when passing through the lumen having a large inner diameter, the insertability and the removability of the insertion section 2 can be improved. As described above, in the endoscope 1 according to this embodiment, the insertion section 2 is inserted or removed in accordance with the inner diameter of the lumen at a part through which the insertion section 2 passes.

Further, in the fin portion 27 in a state that the external force is not exerted in the directions parallel to the longitudinal axis C, the first width dimension T1 of the first width dimension portion 93 is greater than the second width dimension T2 of the second width dimension portion 95. Therefore, a contact area of the fin portion 27 and the paries is increased. Therefore, when the attachment unit 25 rotates, the propulsive force in one of the directions parallel to the longitudinal axis C is further increased. As a result, the insertability and the removability of the insertion section 2 when passing through the lumen having a large inner diameter are further improved.

Furthermore, when the insertion section 2 passes through the lumen having a large inner diameter, since the rotor 61 and the attachment unit 25 rotate in the clockwise direction as seen from the proximal direction, the propulsive force in the distal direction acts on the insertion section 2. As a result, the insertability of the insertion section 2 in the lumen can be improved. On the other hand, when the rotor 61 and the attachment unit 25 rotate in the counterclockwise direction as seen from the proximal direction, the propulsive force toward the proximal direction acts on the insertion section 2. As a result, the removability of the insertion section 2 in the lumen is improved.

Here, in the endoscope disclosed in US2010/0076264, at distal end and proximal end of attachment unit, a gap is provided between the attachment unit and an outer peripheral portion of an insertion section. Therefore, when the attachment unit is rotated with respect to the insertion section, the paries may be possibly sandwiched between the attachment unit and the outer peripheral portion of the insertion section. When the paries is sandwiched between the attachment unit and the outer peripheral part of the insertion section, the insertability and the removability of the insertion section are reduced, and a burden on a patient is increased.

On the other hand, in this embodiment, since the tube distal end portion 28 of the attachment unit 25 is made of a material softer than the tube main body 26, the distal side gap reduction portion 91 is formed on the inner peripheral portion of the tube distal end portion 28. The distal side gap reduction portion 91 eliminates the gap 90 between the attachment unit 25 and the outer peripheral part of the insertion section 2 or the member disposed on the outer peripheral portion of the insertion section 2, or reduces the gap 90 to be smaller than the part to the inner peripheral direction side of the tube main body 26. Therefore, when the propulsive force toward the distal direction is exerted with respect to the insertion section 2 due to the rotation of the attachment unit 25 in the clockwise direction, the paries can be effectively prevented from being sandwiched between the tube distal end portion 28 and the outer peripheral portion of the insertion section 2.

Moreover, since the tube proximal end portion 29 is made of a material softer than the tube main body 26, the proximal side gap reduction portion 92 is formed on the inner peripheral portion of the tube proximal end portion 29. The tube proximal end portion 29 is fixed to the rotor (the second rotor) 61 of the insertion section 2 without the gap 90 by the proximal side gap reduction portion 92. That is, the proximal side gap reduction portion 92 eliminates the gap 90 between the attachment unit 25 and the outer peripheral portion of the insertion section 2 or the member disposed on the outer peripheral portion of the insertion section 2, or reduces the gap 90 to be smaller than the part to the inner peripheral direction side of the tube main body 26. Therefore, when the propulsive force toward the proximal direction is exerted with respect to the insertion section 2 due to the rotation of the attachment unit 25 in the counterclockwise direction, the paries can be effectively prevented from being sandwiched between the tube proximal end portion 29 and the outer peripheral portion of the insertion section 2. As described above, it is possible to effectively avoid sandwiching the paries between the attachment unit 25 and the outer peripheral portion of the insertion section 2.

Additionally, the tube main body 26 of the attachment unit 25 is provided with the gap 90 between itself and the outer peripheral portion of the insertion section 2 or the member disposed on the outer peripheral portion of the insertion section 2 (for example, the adhesive 52). Therefore, rotation properties of the attachment unit 25 with respect to the insertion main body 13 are improved. Accordingly, when the attachment unit 25 rotates, the propulsive force in one of the directions parallel to the longitudinal axis C is further increased. As a result, when passing through the lumen having a large inner diameter, the insertability and the removability of the insertion section 2 are further enhanced.

Further, in the endoscope 1, the tube distal end portion 28 is placed to the outer peripheral direction side of the bending tube connecting portion (the first connecting tube portion) 21 that connects the active bending portion (the first tubular portion 16) to the passive bending portion (the second tubular portion 17). The bending tube connecting portion 21 is less flexible than the active bending portion 16 and the passive bending portion 17, and it is not bent by the external force in the directions perpendicular to the longitudinal axis C. Therefore, even when the active bending portion 16 and the passive bending portion 17 bend, the gap 90 is hardly increased between the tube distal end portion 28 and the outer peripheral portion of the insertion section 2 or the member disposed on the outer peripheral portion of the insertion section 2. Therefore, the paries can be further effectively prevented from being sandwiched between the tube distal end portion 28 and the outer peripheral portion of the insertion section 2.

Further, the tube proximal end portion 29 is placed to the outer peripheral direction side of the flexible tube connecting portion (the second connecting tube portion) 23 that connects the first flexible portion (the third tubular portion) 18 to the second flexible portion (the fourth tubular portion) 19. The flexible tube connecting portion 23 is less flexible than the first flexible portion 18 and the second flexible portion 19, and it is not bent by the external force in the directions perpendicular to the longitudinal axis C. Therefore, even when the first flexible portion 18 and the second flexible portion 19 bend, the gap 90 is hardly increased between the tube proximal end portion 29 and the outer peripheral portion of the insertion section 2 or the member disposed on the outer peripheral portion of the insertion section 2. Therefore, the paries is further effectively prevented from being sandwiched between the tube proximal end portion 29 and the outer peripheral portion of the insertion section 2.

Further, in the small intestine or the large intestine, there are parts where the lumen bends. Therefore, the insertion section (2) must have flexibility to some extent to facilitate passage through the bent parts of the lumen. In the endoscope disclosed in US2010/0076264, the attachment unit is extended over the substantially entire length of the insertion section in the directions parallel to the longitudinal axis. In general, the part on the proximal direction side of the insertion section of the endoscope is the flexible portion. As described above, the flexible portion is less flexible than the passive bending portion that is passively bent by the external force. Therefore, since the attachment unit is placed to the outer peripheral direction side of the flexible portion, the flexibility of the flexible portion is reduced. When the flexibility of the flexible portion is decreased, the insertion section has a difficult in passing through bent parts of the lumen, and the insertability and the removability of the insertion section in the lumen are reduced.

Here, it is possible to consider avoiding a reduction in flexibility of the part on the proximal direction side of the insertion section by extending the passive bending portion to the proximal end of the insertion section to the proximal direction side of the active bending portion without providing the flexible portion to the insertion section. However, in the state that the attachment unit is not rotated, the insertion section is inserted or removed in the lumen by the force in one of the directions parallel to the longitudinal axis applied by an operator. Therefore, with the configuration that the flexibility of the insertion section is reduced as going toward the proximal direction, transmissibility of the force applied by the operator is held. Therefore, in the configuration that the passive bending portion is extended to the proximal end, the flexibility of the part on the proximal direction side of the insertion section is extremely increased. Therefore, in the state that the attachment unit is not rotated, when inserting or removing the insertion section, the transmissibility of the force applied by the operator is reduced.

On the other hand, in this embodiment, the passive bending portion 17 is placed to the proximal direction side of the active bending portion 16, and the first flexible portion 18 and the second flexible portion 19, each being less flexible than the passive bending portion 17, are placed to the proximal direction side of the passive bending portion 17. Further, the attachment unit 25 is extended along the longitudinal axis C from the position to the outer peripheral direction side of the bending tube connecting portion 21 to the position to the outer peripheral direction side of the flexible tube connecting portion 23. That is, a part of the attachment unit 25 is placed to the outer peripheral direction side of the passive bending portion 17. With the above-described configuration, the attachment unit 25 is not placed to the outer peripheral direction side of the second flexible portion 19 provided at the part on the proximal direction side of the insertion section 2. Therefore, a reduction in flexibility of the second flexible portion 19 is avoided. Therefore, the insertion section 2 can readily pass through the bent parts of the lumen, and the insertability and the removability of the insertion section 2 in the lumen can be improved.

Additionally, in the insertion section 2, the first flexible portion 18 and the second flexible portion 19 are provided to the proximal direction side of the passive bending portion 17. Therefore, the flexibility in the part on the proximal direction side of the insertion section 2 is not extremely increased. Therefore, when inserting or removing the insertion section 2 in the state that the attachment unit 25 is not rotated, the force in one of the directions parallel to the longitudinal axis C applied by the operator is appropriately transmitted.

Here, in the state that the attachment unit 25 is attached to the insertion section 2, the flexibility of the second flexible tube portion 19 is greater than that of the first flexible tube portion 18. As described above, in the state that the attachment unit 25 is not rotated, it is preferable for the flexibility of the insertion section to be reduced as going toward the proximal direction. Therefore, in this embodiment, the pulling wire 85 and the coil pipe 89 are provided in the second flexible portion 19. When the pulling wire 85 is pulled, the compression force in the directions parallel to the longitudinal axis C acts on the coil pipe 89. When the compression force acts, the hardness of the coil pipe 89 is increased, and the flexibility of the second flexible portion 19 is reduced. Since the flexibility of the second flexible portion 19 is reduced, when inserting or removing the insertion section 2 in the state that the attachment unit 25 is not rotated, the transmissibility of the force in the directions parallel to the longitudinal axis C applied by the operator is further improved.

Furthermore, when inserting or removing the insertion unit 2 into or from the lumen, the motor 75 as the drive member is driven to rotate. As a result, the attachment unit 25 rotates about the longitudinal axis C, and the propulsive force in one of the directions parallel to the longitudinal axis C acts on the insertion section 2. At this time, a problem, e.g., a failure may possibly occur in the motor 75 so that the motor 75 cannot be driven to rotate. In this case, the attachment unit 25 does not rotate, and the propulsive force in the directions parallel to the longitudinal axis C does not act on the insertion section 2.

Therefore, in this embodiment, when a problem occurs in the motor 75, the switching connecting portion 111 of the gear unit 110 is removed from the motor 75, and the motor 75 is removed from the member inserting portion 72. Further, the manual rotation member 118 is attached to the member inserting portion 72, and the switching connecting portion 111 connects the linear member 83 to the manual rotation member 118. As a result, the gear unit 110 is connected to the manual rotation unit 117. Furthermore, the manual rotation member 118 performs a rotational operation. As a result, the attachment unit 25 rotates, and the propulsive force in one of the directions parallel to the longitudinal axis C acts on the insertion section 2. As described above, in this embodiment, it is possible to appropriately cope with a problem of the motor 75 which is the drive member.

Moreover, the switching connecting portion 111 provided at the end portion of the linear member 83 on the opposite side of the rotary gear 63 selectively connects the linear member 83 to the motor 75 as the drive member or the manual rotation member 118. Therefore, removal of the motor 75 or the manual rotation member 118 from the linear member 83 and connection of the linear member 83 to the motor 75 or the manual rotation member 118 can be facilitated.

Therefore, the endoscope 1 having the above-described configuration exerts the following effects. That is, in the endoscope 1 according to this embodiment, since the tube distal end portion 28 of the attachment unit 25 is made of a material softer than the tube main body 26, the distal side gap reduction portion 91 is formed on the inner peripheral portion of the tube distal end portion 28. The distal side gap reduction portion 91 eliminates the gap 90 between the attachment unit 25 and the outer peripheral portion of the insertion section 2 or the member disposed on the outer peripheral portion of the insertion section 2, or reduces the gap 90 to be smaller than the part to the inner peripheral direction side of the tube main body 26. Therefore, when the propulsive force toward the distal direction acts on the insertion section 2 due to the rotation of the attachment unit 25 in the clockwise direction, the paries can be effectively prevented from being sandwiched between the tube distal end portion 28 and the outer peripheral portion of the insertion section 2.

Additionally, since the tube proximal end portion 29 is made of a material softer than the tube main body 26, the proximal side gap reduction portion 92 is formed on the inner peripheral portion of the tube proximal end portion 29. The tube proximal end portion 29 is fixed to the rotor (the second rotor) 61 of the insertion section 2 without the gap 90 by the proximal side gap reduction portion 92. That is, the proximal side gap reduction portion 92 eliminates the gap 90 between the attachment unit 25 and the outer peripheral portion of the insertion section 2 or the member disposed on the outer peripheral portion of the insertion section 2, or reduces the gap 90 to be smaller than the part to the inner peripheral direction side of the tube main body 26. Therefore, when the propulsive force in the proximal direction acts on the insertion section 2 due to the rotation of the attachment unit 25 in the counterclockwise direction, the paries can be effectively prevented from being sandwiched between the tube proximal end portion 29 and the outer peripheral portion of the insertion section 2. As described above, in the endoscope 1, it is possible to effectively avoid sandwiching the paries between the attachment unit 25 and the outer peripheral portion of the insertion section 2.

Furthermore, in the endoscope 1, the tube main body 26 of the attachment unit 25 is provided with the gap 90 between itself and the outer peripheral portion of the insertion section 2 or the member disposed on the outer peripheral portion of the insertion section 2. Therefore, the rotation properties of the attachment unit 25 with respect to the insertion main body 13 can be improved. Therefore, when the attachment unit 25 rotates, the propulsive force in one of the directions parallel to the longitudinal axis C is increased. Therefore, when passing through the lumen having a large inner diameter, the insertability and the removability of the insertion section 2 can be improved.

Moreover, in the endoscope 1, the tube distal end portion 28 is placed to the outer peripheral direction side of the bending tube connecting portion (the first connecting tube portion) 21 that connects the active bending portion (the first tubular portion) 16 with the passive bending portion (the second tubular portion) 17. The bending tube connecting portion 21 is less flexible than the active bending portion 16 and the passive bending portion 17, and it is not bent by the external force in the directions perpendicular to the longitudinal axis C. Therefore, even when the active bending portion 16 and the passive bending portion 17 bend, the gap 90 is hardly increased between the tube distal end portion 28 and the outer peripheral portion of the insertion section 2 or the member disposed on the outer peripheral portion of the insertion section 2. Therefore, the paries can be further effectively prevented from being sandwiched between the tube distal end portion 28 and the outer peripheral portion of the insertion section 2.

Additionally, in the endoscope 1, the tube proximal end portion 29 is placed to the outer peripheral direction side of the flexible tube connecting portion (the second connecting tube portion) 23 that connects the first flexible portion (the third tubular portion) 18 to the second flexible portion (the fourth tubular portion) 19. The flexible tube connecting portion 23 is less flexible than the first flexible portion 18 and the second flexible portion 19, and it is not bent by the external force in the directions perpendicular to the longitudinal axis C. Therefore, even when the first flexible portion 18 and the second flexible portion 19 bend, the gap 90 is hardly increased between the tube proximal end portion 29 and the outer peripheral portion of the insertion section 2 and the member disposed on the outer peripheral portion of the insertion section 2. Therefore, the paries can be further effectively prevented from being sandwiched between the tube proximal end portion 29 and the outer peripheral portion of the insertion section 2.

Further, in the endoscope 1, the dimension (D1 or D2) from the longitudinal axis C to the outer peripheral end of the fin portion 27 varies in accordance with the state of exertion of the external force in the directions parallel to the longitudinal axis C. In the state that the attachment unit 25 is not rotated, when inserting or removing the insertion section 2 into or from the lumen, the operator applies the force in one of the directions parallel to the longitudinal axis C. Therefore, when the insertion section 2 passes through the lumen having a small inner diameter, the external force in one of the directions parallel to the longitudinal axis C acts on the fin portion 27 from the paries. The second width dimension portion 95 of the fin portion 27 bends by the external force from the paries.

As a result, the dimension from the longitudinal axis C to the outer peripheral end of the fin portion 27 is reduced to dimension D2. Therefore, the insertion section 2 can readily pass through the lumen having the small inner diameter.

Furthermore, in the endoscope 1, when the insertion section 2 passes through the lumen having a large inner diameter, the external force in the directions parallel to the longitudinal axis C is not exerted with respect to the fin portion 27. Therefore, the second width dimension portion 95 of the fin portion 27 does not bend, and the dimension from the longitudinal axis C to the outer peripheral end of the fin portion 27 is dimension D1 greater than dimension D2. At this time, the first width dimension portion 93 of the fin portion 27 comes into contact with the paries. When the attachment unit 25 rotates in this state, the propulsive force in one of the directions parallel to the longitudinal axis C acts on the insertion section 2. With the propulsive force, when passing through the lumen having the large inner diameter, the insertability and the removability of the insertion section 2 can be improved. As described above, in the endoscope 1, the insertion section 2 can be inserted or removed in accordance with the inner diameter of the lumen at a part through which the insertion section 2 passes.

Moreover, in the endoscope 1, in the state that the external force does not act on the fin portion 27 in the directions parallel to the longitudinal axis C, the first width dimension T1 of the first width dimension portion 93 is greater than the second width dimension T2 of the second width dimension portion 95. Therefore, a contact area of the fin portion 27 and the paries is increased. Therefore, when the attachment unit 25 rotates, the propulsive force in one of the directions parallel to the longitudinal axis C is further increased. As a result, it is possible to further improve the insertability and the removability of the insertion section 2 when passing through the lumen having the large inner diameter.

Additionally, in the endoscope 1, the passive bending portion 17 is placed to the proximal direction side of the active bending portion 16, and the first flexible portion 18 and the second flexible portion 19, having the flexibilities lower than that of the passive bending portion 17, are placed to the proximal direction side of the passive bending portion 17. Further, the attachment unit 25 is extended from the position to the outer peripheral direction side of the bending tube connecting portion 21 to the position to the outer peripheral direction side of the flexible tube connecting portion 23 along the longitudinal axis C. That is, a part of the attachment unit 25 is placed to the outer peripheral direction side of the passive bending portion 17. With the above-described configuration, the attachment unit 25 is not placed to the outer peripheral direction side of the second flexible portion 19 provided in the region on the proximal direction side of the insertion section 2. Accordingly, a reduction in flexibility of the second flexible portion 19 is avoided. Therefore, the insertion section 2 can easily pass through the bent parts of the lumen, and the insertability and the removability of the insertion section 2 in the lumen can be improved.

Further, in the endoscope 1, the first flexible portion 18 and the second flexible portion 19 are provided to the proximal direction side of the passive bending portion 17. Therefore, the flexibility in the region on the proximal direction side of the insertion section 2 is not extremely increased. Therefore, when inserting or removing the insertion section 2 in the state that the attachment unit 25 is not rotated, the force in one of the directions parallel to the longitudinal axis C applied by the operator can be appropriately transmitted.

Furthermore, in the endoscope 1, the pulling wire 85 and the coil pipe 89 are provided in the second flexible portion 19. When the pulling wire 85 is pulled, the compression force in the directions parallel to the longitudinal axis C acts on the coil pipe 89. When the compression force acts, the hardness of the coil pipe 89 is increased, and the flexibility of the second flexible portion 19 is reduced. Since the flexibility of the second flexible portion 19 is reduced, when inserting or removing the insertion section 2 in the state that the attachment unit 25 is not rotated, the transmissibility of the force in one of the directions parallel to the longitudinal axis C applied by the operator can be further improved.

Moreover, in the endoscope 1, the rotary gear 63 and the gear portion 65 of the rotor 61 are separated from the built-in extended members 33 in the insertion main body 13 by the connecting mouth ring (the partition member) 58 provided in the flexible tube connecting portion 23. As a result, the rotary gear 63 and the gear portion 65 can be effectively prevented from coming into contact with the built-in extended members 33.

Additionally, in the endoscope 1, the water-tightness is maintained between the rotor 61 and the connecting mouth ring 58 by the elastic member 62. As a result, inflow of a liquid into the gear arrangement cavity 64 from the outside of the insertion section 2 is avoided. Therefore, inflow of the liquid into the insertion main body 13, where the built-in extended members 33 are provided, is avoided.

Further, in the endoscope 1, the proximal end of the protective tube 37, that covers each built-in extended member 33, is placed to the distal direction side of the flexible tube connecting portion 23 to which the rotary gear 63 is disposed. That is, the proximal end of the protective tube 37 is placed to the distal direction side of the rotary gear 63. The rotary gear 63, the rotor 61, and others as members that rotate the attachment unit 25 are attached to the flexible tube connecting portion 23. Therefore, an inner diameter of the flexible tube connecting portion 23 (the connecting mouth ring 58) is smaller than an inner diameter of the passive bending portion 17, an inner diameter of the first flexible portion 18, and others. Therefore, when the proximal end of the protective tube 37, that covers each built-in extended member 33, is placed to the distal direction side of the flexible tube connecting portion 23, a space in the flexible tube connecting portion 23 is assured.

In the endoscope 1, the drive unit 113 or the manual rotation unit 117 is selectively connected to the gear unit 110 including the rotary gear 63. Therefore, when a problem occurs in the motor 75, the switching connecting portion 111 of the gear unit 110 is removed from the motor 75, and the motor 75 is removed from the member inserting portion 72. Further, the manual rotation member 118 is attached to the member inserting portion 72, and the switching connecting portion 111 connects the linear member 83 to the manual rotation member 118. Furthermore, the manual rotation member 118 performs a rotational operation. As a result, the attachment unit 25 rotates, and the propulsive force in one of the directions parallel to the longitudinal axis C functions with respect to the insertion section 2. As described above, in the endoscope 1, it is possible to appropriately cope with a problem of the motor 75 which is the drive member.

Moreover, in the endoscope 1, the switching connecting portion 111 provided at the end portion of the linear member 83 on the opposite side of the rotary gear 63 selectively connects the linear member 83 to the motor 75 as the drive member or the manual rotation member 118. Therefore, removal of the motor 75 or the manual rotation member 118 from the linear member 83 and connection of the linear member 83 to the motor 75 or the manual rotation member 118 can be facilitated.

Additionally, in the endoscope 1, the elastic member 123 maintains water-tightness between the member inserting portion 72 and the motor 75 or the manual rotation member 118 attached to the member inserting portion 72. As a result, inflow of a liquid into the operation section 3 from the outside is avoided. With the above-described configuration, the motor 75 or the manual rotation member 118 can be cleaned and sterilized while being attached to the member inserting portion 72.

Modification of First Embodiment

Figure 9:
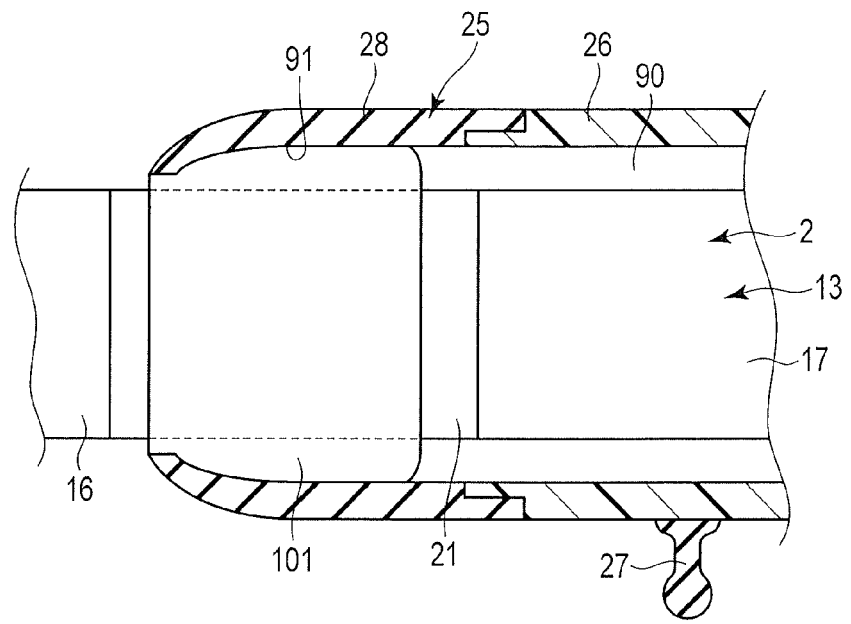
FIG. 9 is a schematic view showing an insertion section and an attachment unit near a bending tube connecting portion of an endoscope according to a first modification of the first embodiment.

It is to be noted that, in the first embodiment, the insertion section 2 includes the rotor (the second rotor) 61 to which the tube proximal end portion 29 is fixed without a gap. However, as a first modification, as shown in FIG. 9, the insertion section 2 may include a rotor (a first rotor) 101 to which the tube distal end portion 28 is fixed without a gap. The rotor 101 can rotate about the longitudinal axis C with respect to the insertion main body 13. The principle of rotating the rotor 101 is the same as that of the rotor 61, and hence a description thereof will be omitted. The tube distal end portion 28 is fixed to the rotor (the first rotor) 101 of the insertion section 2 without the gap 90 by the distal side gap reduction portion 91 of the tube distal end portion 28.

Further, in this modification, the rotor 101 is provided to the bending tube connecting portion 21. Therefore, the tube distal end portion 28 is placed to the outer peripheral direction side of the bending tube connecting portion (the first connecting tube portion) 21 that connects the active bending portion (the first tubular portion) 16 to the passive bending portion (the second tubular portion) 17. The bending tube connecting portion 21 is less flexible than the active bending portion 16 and the passive bending portion 17, and it is not bent by the external force in the directions perpendicular to the longitudinal axis C. Therefore, in this modification, likewise, when the active bending portion 16 and the passive bending portion 17 bend, the gap 90 is hardly increased between the tube distal end portion 28 and the outer peripheral portion of the insertion section 2 or the member disposed on the outer peripheral portion of the insertion section 2.

Further, both rotor (the first rotor) 101 and the rotor (the second rotor) 61 may be provided. Therefore, providing at least one of the rotor (the first rotor) 101 and the rotor (the second rotor) 61 can suffice.

Figure 10:
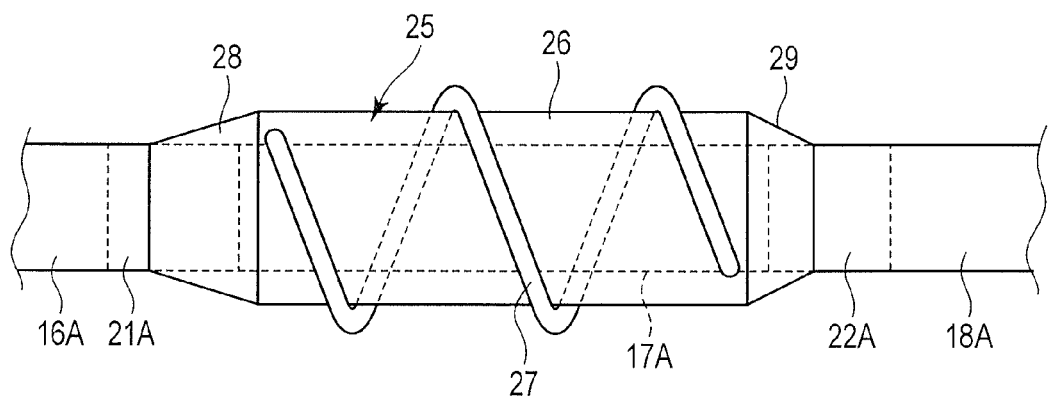
FIG. 10 is a schematic view showing an insertion section and an attachment unit of an endoscope according to a second modification of the first embodiment.

Furthermore, in the first embodiment, the attachment unit 25 is extended from the position to the outer peripheral direction side of the bending tube connecting portion 21 to the position to the outer peripheral direction side of the flexible tube connecting portion 23 along the longitudinal axis C. However, as a second modification, as shown in FIG. 10, the attachment unit 25 may be extended from a position to the outer peripheral direction side of a bending tube connecting portion 21 to a position to the outer peripheral direction side of an intermediate connecting portion 22A along the longitudinal axis C. In this modification, the insertion main body 13 includes an active bending portion 16A, a passive bending portion 17A provided to the proximal direction side of the active bending portion 16A, and a flexible portion 18A provided to the proximal direction side of the passive bending portion 17A. The active bending portion 16A is connected to the passive bending portion 17A through the bending tube connecting portion 21A. The passive bending portion 17A is connected to the flexible portion 18A through the intermediate connecting portion 22A. The flexible portion 18A is extended to a proximal end of the insertion section 2 along the longitudinal axis C.

Here, the configuration of the active bending portion 16A is substantially the same as the active bending portion 16 according to the first embodiment, the configuration of the passive bending portion 17A is substantially the same as the passive bending portion 17 according to the first embodiment, and the configuration of the flexible portion 18A is substantially the same as the first flexible portion 18 according to the first embodiment. Moreover, the configuration of the bending tube connecting portion 21A is substantially the same as the bending tube connecting portion 21 according to the first embodiment, and the configuration of the intermediate connecting portion 22A is substantially the same as the intermediate connecting portion 22 according to the first embodiment. Therefore, a description on the configurations of the active bending portion 16A, the passive bending portion 17A, the flexible portion 18A, the bending tube connecting portion 21A, and the intermediate connecting portion 22A will be omitted.

In this modification, the active bending portion 16A functions as a first tubular portion, and the passive bending portion 17A functions as a continuous body of a second tubular portion and a third tubular portion. Furthermore, the flexible portion 18A serves as a fourth tubular portion. Moreover, the bending tube connecting portion 21A serves as a first connecting tube portion that connects the first tubular portion (16A) with the second tubular portion (17A). Moreover, the intermediate connecting portion 22A serves as a second connecting tube portion that connects the third tubular portion (17A) with the fourth tubular portion (18A).

In this modification, the tube distal end portion 28 is placed to the outer peripheral direction side of the bending tube connecting portion (the first connecting tube portion) 21A that connects the active bending portion (the first tubular portion) 16A to the passive bending portion (the second tubular portion) 17A. The bending tube connecting portion 21A is less flexible than the active bending portion 16A and the passive bending portion 17A, and it is not bent by the external force in the directions perpendicular to the longitudinal axis C. Therefore, in this modification, likewise, when the active bending portion 16A and the passive bending portion 17A bend, the gap 90 is hardly increased between the tube distal end portion 28 and the outer peripheral portion of the insertion section 2 or the member disposed on the outer peripheral portion of the insertion section 2.

Furthermore, the tube proximal end portion 29 is placed to the outer peripheral direction side of the intermediate connecting portion (the second connecting tube portion) 22A that connects the passive bending portion (the third tubular portion) 17A to the flexible portion (the fourth tubular portion) 18A. The intermediate connecting portion 22A is less flexible than the passive bending portion 17A and the flexible portion 18A, and it is not bent by the external force in the directions perpendicular to the longitudinal axis C. Therefore, in this modification, likewise, when the passive bending portion 17A and the flexible portion 18A bend, the gap 90 is hardly increased between the tube proximal end portion 29 and the outer peripheral portion of the insertion section 2 or the member disposed on the outer peripheral portion of the insertion section 2.

Moreover, in this modification, the attachment unit 25 is extended along the longitudinal axis C from the position to the outer peripheral direction side of the bending tube connecting portion 21A to the position to the outer peripheral direction side of the intermediate connecting portion 22A. That is, the substantially entire attachment unit 25 is placed to the outer peripheral direction side of the passive bending portion 17A. With the above-described configuration, the attachment unit 25 is not placed to the outer peripheral direction side of the flexible portion 18A provided in the part on the proximal direction side of the insertion section 2. Therefore, the flexibility of the flexible portion 18A can be prevented from being reduced.

Therefore, based on the second modification, to avoid a reduction in flexibility of the part on the proximal direction side of the insertion section 2, placing at least a part of the attachment unit 25 to the outer peripheral direction side of the passive bending portion (17 or 17A) can suffice.

Figure 11A:
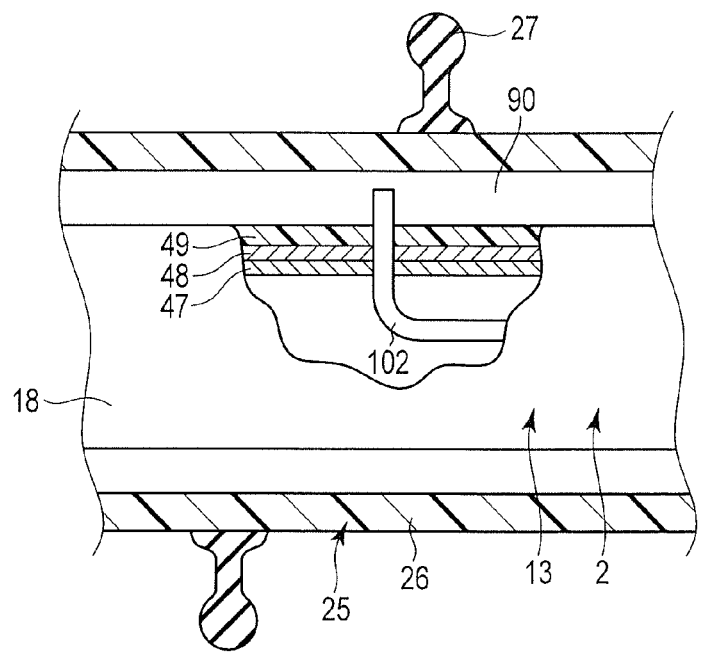
FIG. 11A is a partially cross-sectional schematic view showing an insertion section and an attachment unit near a first flexible portion of an endoscope according to a third modification of the first embodiment.
Figure 11B:
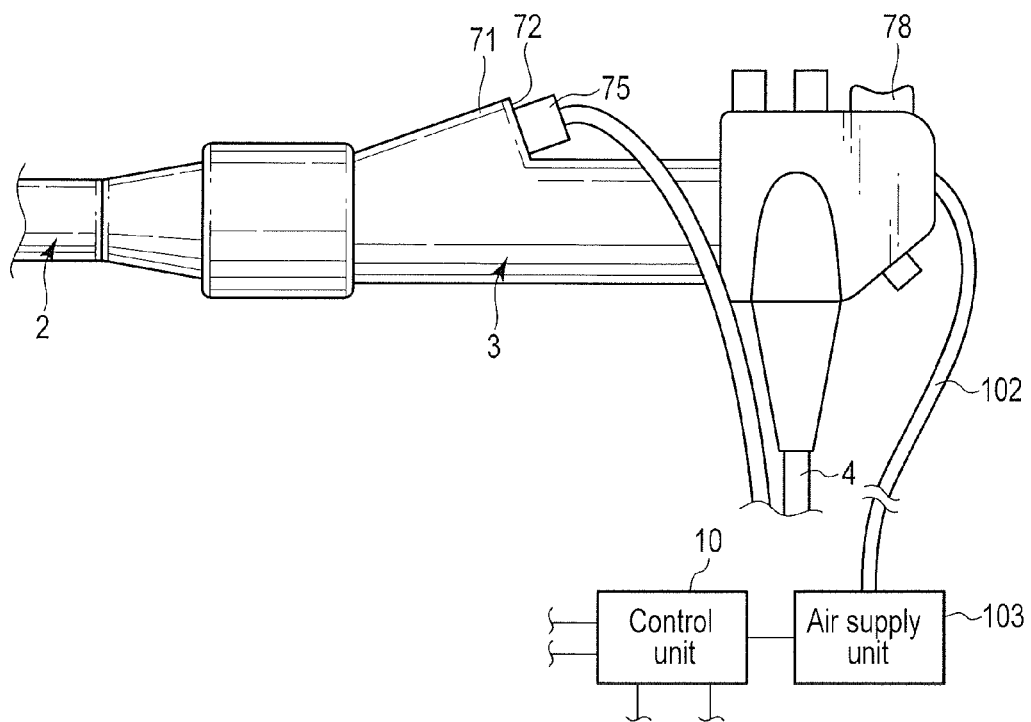
FIG. 11B is a schematic view showing an operation section of an endoscope according the third modification of the first embodiment.

Additionally, as a third modification, as shown in FIG. 11A and FIG. 11B, an air supply tube 102 configured to supply air to the gap 90 between the tube main body 26 and the outer peripheral portion of the insertion section 2 and to suck air from the gap 90 may be provided. The air supply tube 102 is extended to the outside of the operation section 3 from the gap 90 through the outer peripheral portion of the first flexible portion 18, the inside of the insertion main body 13 (the insertion section 2), and the inside of the operation section 3. Further, the other end of the air supply tube 102 is connected to an air supply unit 103. The air supply unit 103 is electrically connected to the control unit 10. When the air supply unit 103 is driven, air supply to the gap 90 and air suction from the gap 90 are carried out. With the air supply and the air suction in the gap 90, the dimension (D1 or D2) from the longitudinal axis C to the outer peripheral end of the fin portion 27 varies. As a result, the dimension (D1 or D2) from the longitudinal axis C to the outer peripheral end of the fin portion 27 is adjusted in accordance with an inner diameter of the lumen. Therefore, in each of the lumens having various inner diameters, the outer peripheral end of the fin portion 27 can be brought into contact with the paries.

Additionally, as a fourth modification, as shown in FIG. 12, two different types of attachment units 25A and 25B may be selectively attached to the insertion section 2. The attachment unit (a first attachment unit) 25A has a dimension L1 in the directions parallel to the longitudinal axis C. Further, in a state that the external force in the directions parallel to the longitudinal axis C is not exerted, the dimension of attachment unit 25A from the longitudinal axis C to the outer peripheral end of the fin portion 27 is D3. The attachment unit (a second attachment unit) 25B has a dimension L2 smaller than dimension L1 in the directions parallel to the longitudinal axis C. Furthermore, in the state that the external force in the directions parallel to the longitudinal axis C is not exerted, the dimension of attachment unit 25B from the longitudinal axis C to the outer peripheral end of the fin portion 27 is a dimension D4 greater than dimension D3. When such a configuration is adopted, the attachment unit (25A or 25B) can be selectively attached to the insertion section 2 in accordance with a type of patient or a type of lumen.

Moreover, as a fifth modification, as shown in FIG. 13, two fin portions 27A and 27B may be spirally extended on the outer peripheral portion of the tube main body 26 of the attachment unit 25. Here, an acute angle α1 of the fin portion (a first fin portion) 27A with respect to the longitudinal axis C is the same as an acute angle α2 of the fin portion (a second fin portion) 27B with respect to the longitudinal axis C. Additionally, the fin potion 27A is apart from the fin portion 27B in the directions parallel to the longitudinal axis C by a distance corresponding to a dimension S, and it is extended at the same pitch as that of the fin portion 27B. As a result, the fin portion 27A and the fin portion 27B are extended without overlapping.

When the two fin portions 27A and 27B are provided, a contact area between the fin portions 27A and 27B and the paries is increased. Therefore, when the attachment unit 25 rotates, the propulsive force in one of the directions parallel to the longitudinal axis C is further increased. As a result, the insertability and the removability of the insertion section 2 when passing through the lumen are further improved.

Further, as a sixth modification, as shown in FIG. 14, two attachment units 25C and 25D may be attached to the insertion section 2 at the same time. In this modification, an attachment unit (a second attachment unit) 25D is provided to the proximal direction side of an attachment unit (a first attachment unit) 25C. When the number of the attachment units 25C and 25D attached to the insertion section 2 is increased, propulsive force in one of the directions parallel to the longitudinal axis C is further increased at the time of simultaneous rotation of the attachment units 25C and 25D. As a result, the insertability and the removability of the insertion section 2 when passing through the lumen are further improved.

Furthermore, in the first embodiment, the tube main body 26 of the attachment unit 25 is made of a resin, and the fin portion 27 is formed of rubber, but the present invention is not restricted thereto. For example, as a seventh modification, as shown in FIG. 15, the tube main body 26 may include a metal helical tube 105, a metal reticular tube 106 that covers the outer peripheral direction side of the helical tube 105, and a resin envelope 107 that covers the outer peripheral direction side of the reticular tube 106. That is, the tube main body 26 has the same layer configuration as the first flexible portion 18 and the second flexible portion 19. In this modification, the fin portion 27 is made of a resin, and it is integrally formed of the envelope 107 of the tube main body 26.

Figure 16:
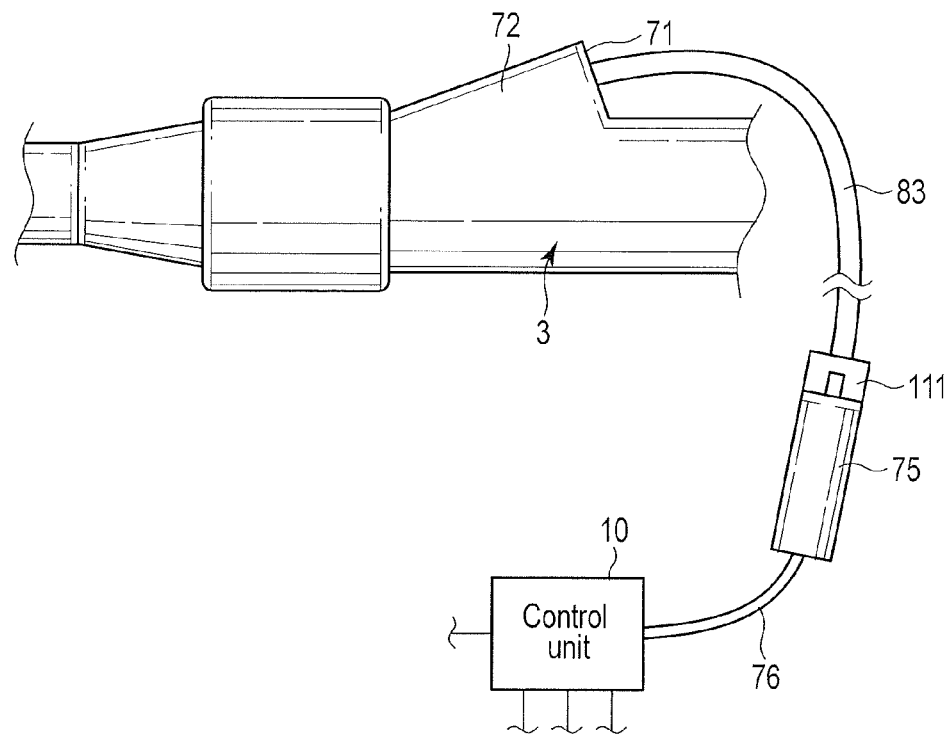
FIG. 16 is a schematic view showing a connecting state of a gear unit and a drive unit of an endoscope according to an eighth modification of the first embodiment.

Further, in the first embodiment, the motor 75 or the manual rotation member 118 is attached to the member inserting portion 72, but the present invention is not restricted thereto. For example, as an eighth modification, as shown in FIG. 16, the linear member 83 may be extended to an outside of the operation section 3 from the member insertion opening 71. In this modification, the linear member 83 is selectively connected to the motor 75 or the manual rotation member 118 outside the operation section 3.

Second Embodiment

A second embodiment according to the present invention will now be described with reference to FIG. 17 and FIG. 18. The second embodiment is obtained by modifying the configuration of the first embodiment as follows. It is to be noted that like reference numerals denote parts equal to those in the first embodiment and a description thereof will be omitted.

Figure 17:
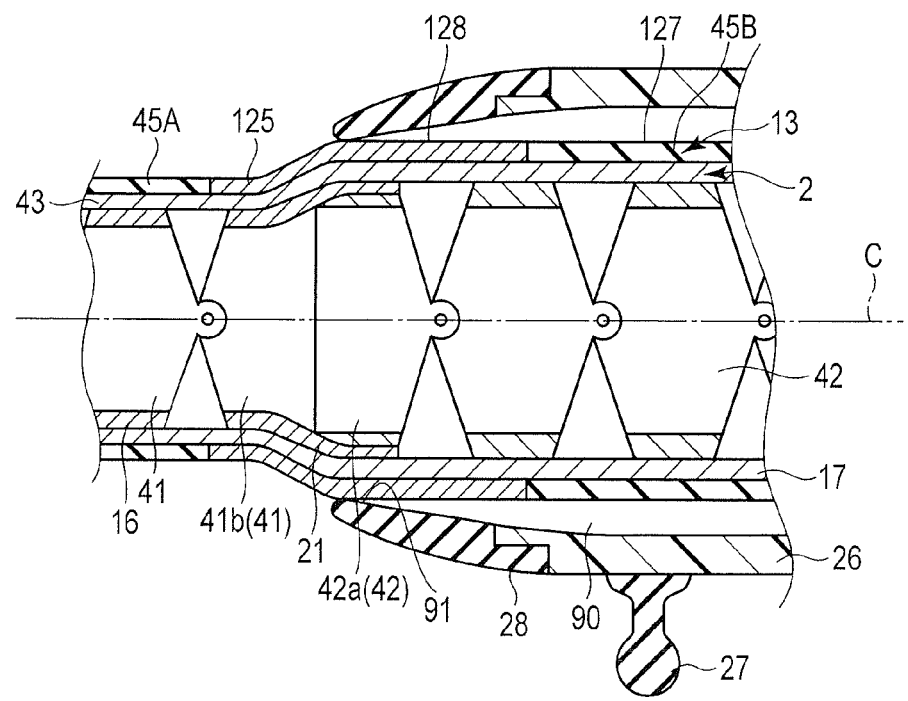
FIG. 17 is a cross-sectional view schematically showing a configuration of an insertion section and an attachment unit near a passive bending portion of an endoscope according to a second embodiment of the present invention.

FIG. 17 is a view showing a configuration of an insertion section 2 and an attachment unit 25 near a bending tube connecting portion 21. As shown in FIG. 17, an insertion main body 13 according to this embodiment includes a first bending portion envelope 45A and a second bending portion envelope 45B. In an active bending portion 16, the first bending portion envelope 45A covers an outer peripheral direction side of a bending portion reticular tube 43. Furthermore, in a passive bending portion 17, the second bending portion envelope 45B covers the outer peripheral direction side of the bending portion reticular tube 43. A metal intermediate envelope 125 is provided between the first bending portion envelope 45A and the second bending portion envelope 45B. In the bending tube connecting portion 21, the intermediate envelope 125 covers the outer peripheral direction side of the bending portion reticular tube 43.

In this embodiment, a first outer surface portion 127 of the insertion main body 13 is formed of the first bending portion envelope 45A and a first flexible portion envelope 49. A tube main body 26 of the attachment unit 25 is placed to the outer peripheral direction side of the first outer surface portion 127. Moreover, a second outer surface portion 128 of the insertion main body 13 is formed of the intermediate envelope 125. A tube distal end portion 28 of the attachment unit 25 is placed to the outer peripheral direction side of the second outer surface portion 128. The first bending portion envelope 45A is made of, for example, fluorine-containing rubber, and the first flexible portion envelope 49 made of a resin, whereas the intermediate envelope 125 is made of a metal. Therefore, the second outer surface portion 128 has higher strength against friction than the first outer surface portion 127.

In the tube distal end portion 28, a distal side gap reduction portion 91 eliminates a gap 90 between the attachment unit 25 and the outer peripheral portion of the insertion section 2 or a member disposed on the outer peripheral portion of the insertion section 2, or reduces the gap 90 to be smaller than the part to the inner peripheral direction side of the tube main body 26. Therefore, when the attachment unit 25 rotates, friction is apt to occur between the tube distal end portion 28 and the second outer surface portion 128. Therefore, in this embodiment, the strength of the second outer surface portion 128 against friction is increased by providing the intermediate envelope 125. Therefore, the second outer surface portion 128 is hardly damaged by the friction produced when the attachment unit 25 rotates.

Additionally, the metal intermediate envelope 125 (the second outer surface portion 128) is placed to the bending tube connecting portion 21 (a first connecting tube portion) less flexible than the active bending portion (a first tubular portion) 16 and the passive bending portion 17 (a second tubular portion). The bending tube connecting portion 21 is not bent by the external force in the directions perpendicular to the longitudinal axis C. Therefore, quality of the intermediate envelope 125 can be readily maintained.

Figure 18:
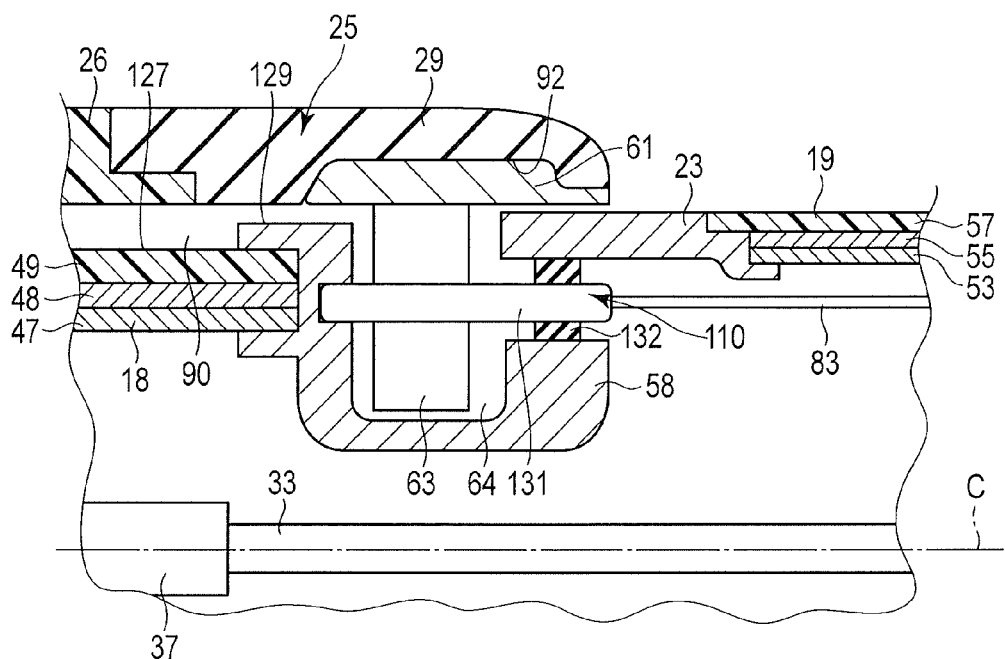
FIG. 18 is a cross-sectional view schematically showing the configuration of the insertion section and the attachment unit near a flexible tube connecting portion of the endoscope according to the second embodiment.

FIG. 18 is a view showing a configuration of the insertion section 2 and the attachment unit 25 near a flexible tube connecting portion 23. As shown in FIG. 18, like the first embodiment, a metal connecting mouth ring 58 that connects a first flexible portion 18 to a second flexible portion 19 is provided to the flexible tube connecting portion 23. A third outer surface portion 129 of the insertion main body 13 is formed of the connecting mouth ring 58. A tube proximal end portion 29 of the attachment unit 25 is placed to the outer peripheral direction side of the third outer surface portion 129. Since the connecting mouth ring 58 is made of a metal, the third outer surface portion 129 has higher strength against friction than the first outer surface portion 127.

Like the first embodiment, a rotor (a second rotor) 61 and a rotary gear 63 are attached to the connecting mouth ring 58. The connecting mouth ring 58 functions as a partition member configured to separate the rotary gear 63 and a gear portion 65 of the rotor 61 from each built-in extended member 33. A gear arrangement cavity 64, in which the rotary gear 63 is placed, is formed between the rotor 61 and the connecting mouth ring 58. A linear member 83 is extended in the insertion main body 13 (the insertion section 2) and the operation section 3. One end of the linear member 83 is connected to a motor 75 attached to a member insertion portion 72. It is to be noted that, as different from the first embodiment, a channel tube 69 is not provided and a channel 73 is not formed in this embodiment.

A gear connecting portion 131 that connects the rotary gear 63 to the linear member 83 is provided at the other end of the linear member 83. The gear connecting portion 131 connects the rotary gear 63 with the linear member 83 in the gear arrangement cavity 64. Furthermore, the gear connecting portion 131 is attached to the connecting mouth ring 58 through an elastic member 132. When the elastic member 132 maintains the water-tightness between the gear connecting portion 131 and the connecting mouth ring 58, inflow of a liquid into the insertion main body 13 from the gear arrangement cavity 64 can be avoided.

Here, the elastic member 132 is smaller than the elastic member 62 according to the first embodiment that maintains the water-tightness between the rotor 61 and the connecting mouth ring 58. Therefore, when the attachment unit 25 rotates, friction between the gear connecting portion 131 and the elastic member 132 is smaller than friction generated between the rotor 61 and the elastic member 62 in the first embodiment. Therefore, as compared with the first embodiment, drive force of rotating the attachment unit 25 can be decreased.

Additionally, in a tube proximal end portion 29, a proximal side gap reduction portion 92 eliminates the gap 90 between the attachment unit 25 and the outer peripheral portion of the insertion section 2 or a member disposed on the outer peripheral portion of the insertion section 2, or reduces the gap 90 to be smaller than a part to the inner peripheral direction side of the tube main body 26. Further, the rotor 61 rotates with respect to the connecting mouth ring 58. Therefore, when the attachment unit 25 rotates, friction is apt to occur between the tube proximal end portion 29 and the rotor 61, and, the third outer surface portion 129. Therefore, in this embodiment, the strength of the third outer surface portion 129 against friction is increased by providing the connecting mouth ring 58. Therefore, the third outer surface portion 129 is hardly damaged by friction that occurs when the attachment unit 25 rotates.

Furthermore, since the metal connecting mouth ring 58 (the third outer surface portion 129) is placed to the flexible tube connecting portion 23 (a second connecting tube portion) less flexible than the first flexible portion (a third tubular portion) 18 and the second flexible portion 19 (a fourth tubular portion). The flexible tube connecting portion 23 is not bent by the external force in the directions perpendicular to the longitudinal axis C. Therefore, quality of the connecting mouth ring 58 can be readily maintained.

Therefore, in the thus configured endoscope 1, in addition to the same effects as those of the first embodiment, the following effects are exerted. That is, in the tube distal end portion 28 of the endoscope 1, the distal side gap reduction portion 91 eliminates the gap 90 between the attachment unit 25 and the outer peripheral portion of the insertion section 2 or the member disposed on the outer peripheral portion of the insertion section 2, or reduces the gap 90 to be smaller than the region to the inner peripheral direction side of the tube main body 26. Therefore, when the attachment unit 25 rotates, friction is apt to occur between the tube distal end portion 28 and the second outer surface portion 128. Therefore, the second outer surface portion 128 of the insertion main body 13 has higher strength against friction than the first outer surface portion 127. Therefore, it is possible to effectively avoid damage to the second outer surface portion 128 due to friction that occurs when the attachment unit 25 rotates.

Furthermore, in the tube proximal end portion 29 of the endoscope 1, the proximal side gap reduction portion 92 eliminates the gap 90 between the attachment unit 25 and the outer peripheral portion of the insertion section 2 or the member disposed on the outer peripheral portion of the insertion unit 2, or reduces the gap 90 to be smaller than the part to the inner peripheral direction side of the tube main body 26. Moreover, the rotor 61 rotates with respect to the connecting mouth ring 58. Therefore, when the attachment unit 25 rotates, friction is apt to occur between the tube proximal end portion 29 and the rotor 61, and, the third outer surface portion 129. Therefore, the third outer surface portion 129 of the insertion main body 13 has higher strength against friction than the first outer surface portion 127. Therefore, it is possible to effectively avoid damage of the third outer surface portion 129 due to friction that occurs when the attachment unit 25 rotates.

Additionally, in the endoscope 1, the gear connecting portion 131 connects the rotary gear 63 to the linear member 83 in the gear arrangement cavity 64. Further, the gear connecting portion 131 is attached to the connecting mouth ring 58 through the elastic member 132. When the elastic member 132 maintains the water-tightness between the gear connecting portion 131 and the connecting mouth ring 58, inflow of a liquid from the gear arrangement cavity 64 into the insertion main body 13 can be avoided.

Furthermore, in the endoscope 1, the elastic member 132 is smaller than the elastic member 62 according to the first embodiment that maintains the water-tightness between the rotor 61 and the connecting mouth ring 58. Therefore, when the attachment unit 25 rotates, friction between the gear connecting portion 131 and the elastic member 132 is reduced. Therefore, drive force of rotating the attachment unit 25 can be reduced.

Moreover, in the endoscope 1, the metal intermediate envelope 125 (the second outer surface portion 128) is placed to the bending tube connecting portion 21 (the first connecting tube portion) less flexible than the active bending portion (the first tubular member) 16 and the passive bending portion 17 (the second tubular member). The bending tube connecting portion 21 is not bent by the external force in the directions perpendicular to the longitudinal axis C. Therefore, the quality of the intermediate envelope 125 can be easily maintained. Additionally, the metal connecting mouth ring 58 (the third outer surface portion 129) is placed to the flexible tube connecting portion 23 (the second connecting tube portion) less flexible than the first flexible portion (the third tubular portion) 18 and the second flexible portion 19 (the fourth tubular portion). The flexible tube connecting portion 23 is not bent by the external force in the directions perpendicular to the longitudinal axis C. Therefore, the quality of the metal connecting mouth ring 58 can be easily maintained.

Modification of Second Embodiment

Figure 19:
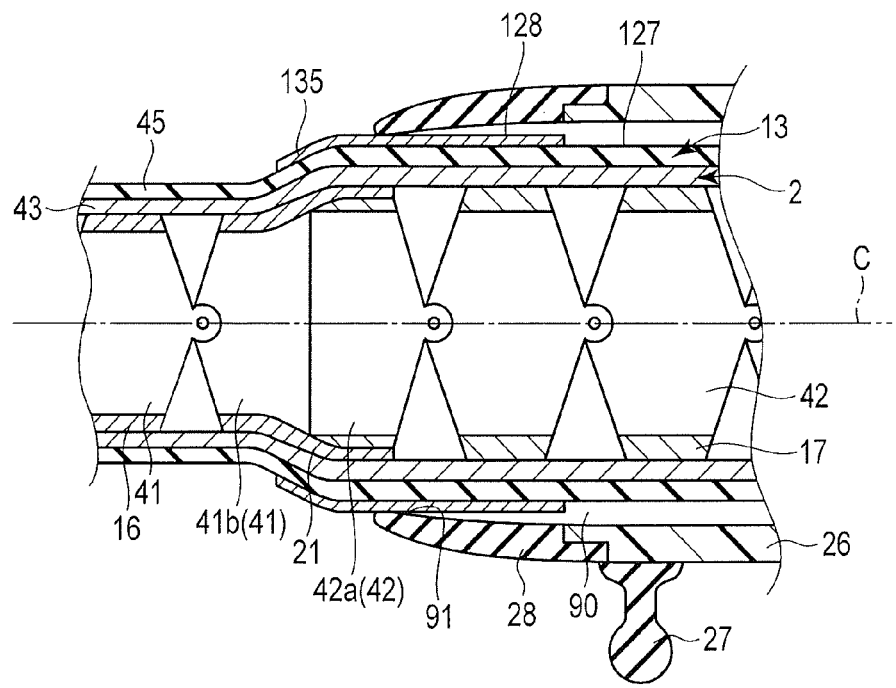
FIG. 19 is a cross-sectional view schematically showing a configuration of an insertion section and an attachment unit near a passive bending portion of an endoscope according to a first modification of the second embodiment.

It is to be noted that the second outer surface portion 128 is formed of the intermediate envelope 125 in the second embodiment, but the present invention is not restricted thereto. For example, as a first modification, as shown in FIG. 19, a metal ring 135 may be fixed to the outer peripheral portion of the bending portion envelope 45. In this case, the second outer surface portion 128, having higher strength against friction than that of the first outer surface portion 127, is formed of the ring 135.

Figure 20:
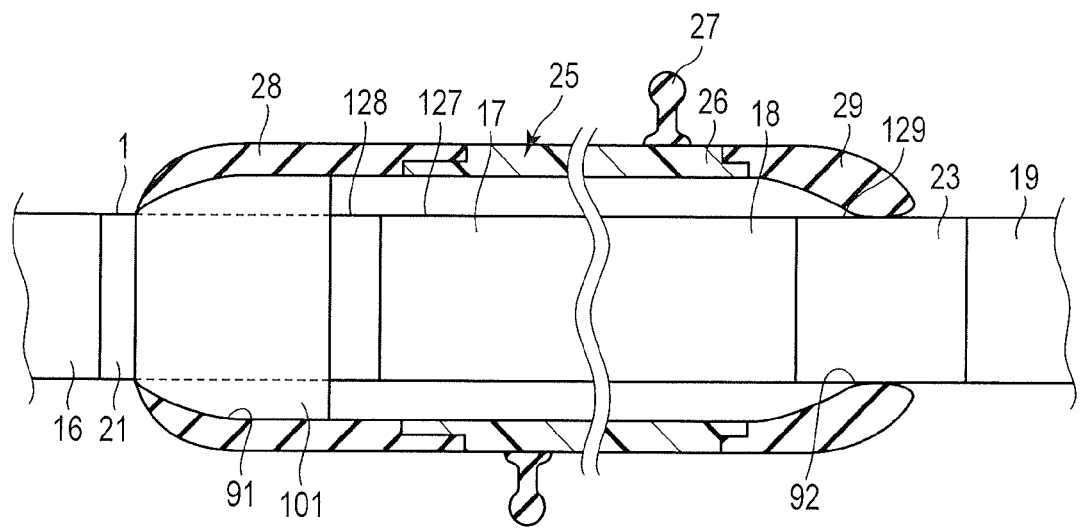
FIG. 20 is a schematic view showing an insertion section and an attachment unit of an endoscope according to a second modification of the second embodiment.

Further, as a second modification, as shown in FIG. 20, the insertion section 2 may includes a rotor (a first rotor) 101 to which the tube distal end portion 28 is fixed without a gap. In this modification, the rotor 101 is placed to the outer peripheral direction side of the second outer surface portion 128. When the attachment unit 25 rotates, friction is apt to occur between the tube distal end portion 28 and the rotor 101, and, the second outer surface portion 128. Therefore, in this modification, strength of the second outer surface portion 128 against friction is set higher than that of the first outer surface portion 127. Therefore, the second outer surface portion 128 is hardly damaged due to friction that occurs when the attachment unit 25 rotates.

Furthermore, when the attachment unit 25 rotates, friction is apt to occur between the tube proximal end portion 29 and the third outer surface portion 129. Therefore, in this modification, strength of the third outer surface portion 129 against friction is set higher than that of the first outer surface portion 127. Therefore, the third outer surface portion 129 is hardly damaged due to friction that occurs when the attachment unit 25 rotates.

Third Embodiment

A third embodiment according to the present invention will now be described with reference to FIG. 21 to FIG. 22. The third embodiment is obtained by modifying the configuration of the first embodiment as follows. It is to be noted that like reference numerals denote parts equal to those in the first embodiment, and a description thereof will be omitted.

Figure 21:
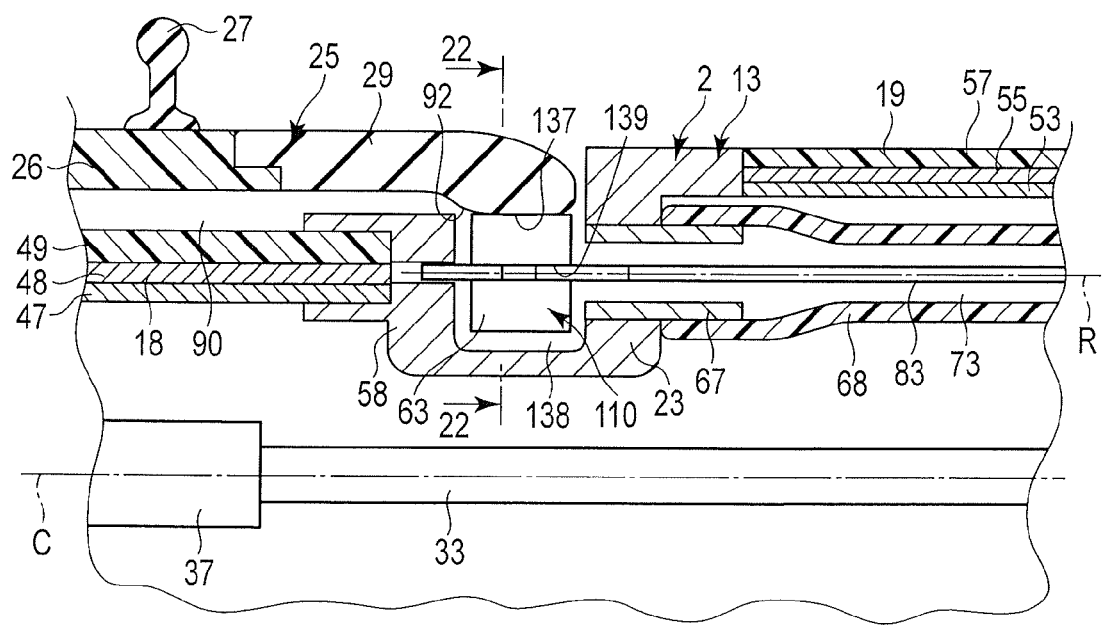
FIG. 21 is a cross-sectional view schematically showing a configuration of an insertion section and an attachment unit near a flexible tube connecting portion of an endoscope according to a third embodiment of the present invention.

FIG. 21 is a view showing a configuration of an insertion section 2 and an attachment unit 25 near a flexible tube connecting portion 23. FIG. 22 is a cross-sectional view taken along a line 22-22 in FIG. 21. As shown in FIG. 21 and FIG. 22, in this embodiment, the insertion section 2 does not include a rotor 61 that rotates about a longitudinal axis C with respect to an insertion main body 13. Further, a gear portion 137 that meshes with a rotary gear 63 of a gear unit 110 is provided to a tube proximal end portion 29 of the attachment unit 25. With such a configuration, the rotary gear 63 is placed on an outer peripheral portion of the insertion section 2, and a gear arrangement portion 138 is provided on the outer peripheral portion of the insertion section 2. That is, in a state that the attachment unit 25 is removed from the insertion section 2, the rotary gear 63 is exposed to the outside.

Furthermore, a groove-shaped portion 139 is provided in the rotary gear 63 along a gear axis R. The groove-shaped portion 139 is formed into a substantially hexagonal shape in a cross section perpendicular to the gear axis R.

In a tube proximal end portion 29, a proximal side gap reduction portion 92 eliminates a gap 90 between the attachment unit 25 and a connecting mouth ring 58 or the rotary gear 63, or reduces the gap 90 to be smaller than a part to an inner peripheral direction side of a tube main body 26. That is, the proximal side gap reduction portion 92 eliminates the gap 90 between the attachment unit 25 and the outer peripheral portion of the insertion section 2 or a member disposed on the outer peripheral portion of the insertion section 2, or reduces the gap 90 to be smaller than the part to the inner peripheral direction side of the tube main body 26. Moreover, the tube proximal end portion 29 meshes with the rotary gear 63 attached to the outer peripheral portion of the insertion section 2 without the gap 90 by the proximal side gap reduction portion 92. Therefore, when the rotary gear 63 rotates about the gear axis R, the attachment unit 25 rotates about the longitudinal axis C with respect to the insertion main body 13.

A connection pipe 67, a channel tube 68, and a member insertion portion 72 define a channel 73 from a gear arrangement portion 138 on the outer peripheral portion of the insertion section 2. That is, the member insertion portion 72, the channel tube 68, and the connection pipe 67 constitute a channel defining portion that defines the channel 73. The channel 73 is extended to the gear arrangement portion 138 from a member insertion opening 71 of an operation section 3. That is, the channel 73 is extended from the outer surface of the operation section 3 through the inside of the operation section 3 and the inside of the insertion section 2 (an insertion main body 13). Additionally, in the gear arrangement portion 138 where the rotary gear 63 is placed, an opening is formed on the outer peripheral portion of the insertion section 2.

In this embodiment, the rotary gear 63 is placed on the outer peripheral portion of the insertion section 2, and the gear arrangement portion 138 is provided on the outer peripheral portion of the insertion section 2. Therefore, in a state that the attachment unit 25 is removed from the insertion section 2, the rotary gear 63 is exposed to the outside. Therefore, the rotary gear 63 can be readily cleaned and sterilized.

Further, the channel 73 is extended from the outer surface of the operation section 3 to the gear arrangement portion 138 on the outer peripheral portion of the insertion section 2. That is, both ends of the channel 73 are opened with respect to the outside of the insertion section 2 and the operation section 3. Therefore, even if a liquid flows into the channel 73, the liquid hardly stays in the channel 73. Therefore, inflow of the liquid into the channel 73 in the insertion main body 13 does not have to be avoided. In this embodiment, since a waterproof elastic member is not provided, when the attachment unit 25 rotates, friction that acts on a linear member 83 and the tube proximal end portion 29 is reduced. Therefore, drive force of rotating the attachment unit 25 can be reduced. Accordingly, a motor 75 as a drive member and the linear member 83 are reduced in size, and the endoscope 1 itself is also reduced in size.

Therefore, in the thus configured endoscope 1, in addition to the same effects as those of the first embodiment, the following effects are exerted. That is, in the endoscope 1, the rotary gear 63 is placed on the outer peripheral portion of the insertion section 2, and the gear arrangement portion 138 is provided on the outer peripheral portion of the insertion section 2. Therefore, in a state that the attachment unit 25 is removed from the insertion section 2, the rotary gear 63 is exposed to the outside. Therefore, the rotary gear 63 can be readily cleaned and sterilized.

Furthermore, the channel 73 is extended from the outer surface of the operation section 3 to the gear arrangement portion 138 on the outer peripheral portion of the insertion section 2. That is, both ends of the channel 73 are opened with respect to the outside of the insertion section 2 and the operation section 3. Therefore, even if a liquid flows into the channel 73, the liquid hardly stays in the channel 73. Therefore, inflow of the liquid into the channel 73 in the insertion main body 13 does not have to be avoided. Since the waterproof elastic member is not provided, when the attachment unit 25 rotates, friction that acts on the linear member 83 and the tube proximal end portion 29 is reduced. Therefore, drive force of rotating the attachment unit 25 can be reduced. Accordingly, the motor 75 as a drive member and the linear member 83 are reduced in size, and the endoscope 1 itself is also reduced in size.

Modification of Third Embodiment

As a first modification of the third embodiment, as shown in FIG. 23, the drive unit 113 or the manual rotation unit 117 may be directly and selectively connected to the rotary gear 63 of the gear unit 110. The drive unit 113 includes a motor 75 as a drive member, and a first linear member 83A. In a state that the motor 75 is attached to a member insertion portion 72 as an attachment portion, the first linear member 83A is extended toward the rotary gear 63 through the inside of the operation section 3 and the inside of the insertion section 2. Further, the drive unit 113 includes a first switching connecting portion 141A that connects the rotary gear 63 to the first linear member 83A in the gear arrangement portion 138. FIG. 24 is a cross-sectional view taken along a line 24-24 in FIG. 23. As shown in FIG. 24, the first switching connecting portion 141A is formed into a substantially hexagonal shape associated with the groove-shaped portion of the rotary gear 63 in the cross section perpendicular to the gear axis R. When the first switching connecting portion 141A is inserted into the groove-shaped portion 139, the rotary gear 63 is connected to the first linear member 83A. As a result, the gear unit 110 is connected to the drive unit 113.

The manual rotation unit 117 includes a manual rotation member 118 and a second linear member 83B. In a state that the manual rotation member 118 is attached to the member insertion portion 72 as the attachment portion, the second linear member 83B is extended toward the rotary gear 63 through the inside of the operation section 3 and the inside of the insertion section 2. Furthermore, the manual rotation unit 117 includes a second switching connecting portion 141B that connects the rotary gear 63 to the second linear member 83B in the gear arrangement portion 138. Like the first switching connecting portion 141A, the second switching connecting portion 141B is formed into a substantially hexagonal shape associated with the groove-shaped portion 139 of the rotary gear 63 in the cross section perpendicular to the gear axis R. When the second switching connecting portion 141B is inserted into the groove-shaped portion 139, the rotary gear 63 is connected to the second linear member 83B. As a result, the gear unit 110 is connected to the manual rotation unit 117.

In this modification, the drive unit 113 or the manual rotation unit 117 is selectively connected to the gear unit 110 including the rotary gear 63. As a result, when a problem occurs in the motor 75, the first switching connecting portion 141A of the drive unit 113 is removed from the rotary gear 63, and the drive unit 113 is removed from the member insertion portion 72. Moreover, the manual rotation member 118 is attached to the member insertion portion 72, and the second linear member 83B is connected to the rotary gear 63 through the second switching connecting portion 141B. Additionally, a rotational operation is carried out in the manual rotation member 118. As a result, the attachment unit 25 rotates, and propulsive force in one of the directions parallel to the longitudinal axis C acts on the insertion section 2. As described above, in the endoscope 1 according to this modification, it is possible to appropriately cope with a problem in the motor 75 which is the drive member. Further, it is also possible to cope with a problem in the first linear member 83A of the drive unit 113.

Fourth Embodiment

A fourth embodiment according to the present invention will now be described with reference to FIG. 25 to FIG. 27. The fourth embodiment is obtained by modifying the configuration of the first embodiment as follows. It is to be noted that like reference numerals denote parts equal to those in the first embodiment, and a description thereof will be omitted.

FIG. 25 is a view showing a configuration of an insertion section 2 and an attachment unit 145 according to this embodiment. As shown in FIG. 25, the attachment unit 145 includes a fin portion 147 spirally extended along a longitudinal axis C. Further, the attachment unit 145 includes a proximal side ring 148 to which a proximal end of the fin portion 147 is fixed, and a distal side ring 149 to which a distal end of the fin portion 147 is fixed.

The proximal side ring 148 is fixed to a rotor 61 without a gap. As a result, the attachment unit 145 rotates about the longitudinal axis C with respect to the insertion main body 13 integrally with the rotor 61 in accordance with rotation of the rotor 61. However, the proximal side ring 148 is restricted so that it cannot move along the longitudinal axis C with respect to the insertion main body 13.

The fin portion 147 includes a metal core 151 spirally extended along the longitudinal axis C, and a rubber portion 152 provided to cover a periphery of the metal core 151. When the metal core 151 is provided, rotation is appropriately transmitted from the proximal side ring 148 to the distal side ring 149. Further, when the metal core 151 is covered with the rubber portion 152, the metal core 151 having high hardness can be prevented from being exposed.

When an external force is exerted in one of directions parallel to the longitudinal axis C, the distal side ring 149 moves along the longitudinal axis C with respect to the insertion section 2 (the insertion main body 13). As a result, a dimension from the longitudinal axis C to an outer peripheral end of the fin portion 147 changes. Furthermore, a dimension of the attachment unit 145 in the directions parallel to the longitudinal axis C also changes. Here, in a state that the external force is not exerted in the directions parallel to the longitudinal axis C, the dimension from the longitudinal axis C to the outer peripheral end of the fin portion 147 is D5.

Figure 26:
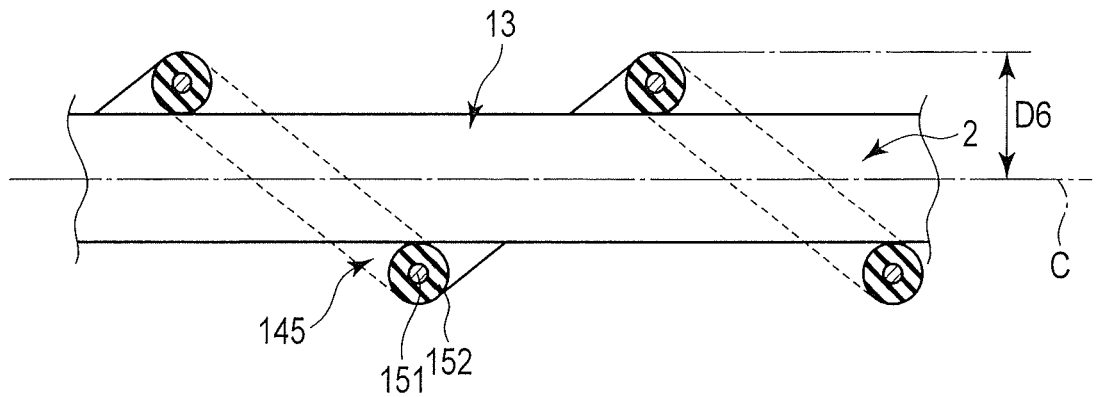
FIG. 26 is a schematic view showing a state that external force acts on a fin portion of the attachment unit of the endoscope according to the fourth embodiment from a proximal direction.

FIG. 26 is a view showing a state that the external force acts on the fin portion 147 from the proximal direction. As shown in FIG. 26, when the external force acts from the proximal direction, the distal side ring 149 moves in the distal direction. As a result, a pitch of the fin portion 147 is increased, and an inner diameter of the attachment unit 145 is reduced. At this time, the dimension from the longitudinal axis C to the outer peripheral end of the fin portion 147 is D6, and it is smaller than dimension D5 in the state that the external force does not act in the directions parallel to the longitudinal axis C. Moreover, the dimension of the attachment unit 145 in the directions parallel to the longitudinal axis C is greater than that in the state that the external force does not act in the directions parallel to the longitudinal axis C.

Figure 27:
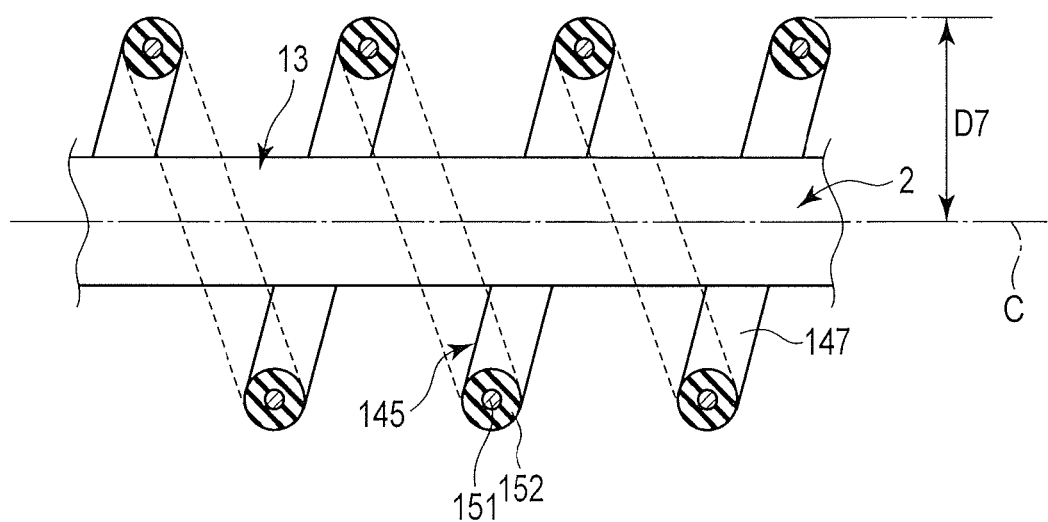
FIG. 27 is a schematic view showing a state that external force acts on the fin portion of the attachment unit of the endoscope according to the fourth embodiment from a distal direction.

FIG. 27 is a view showing a state that the external force acts on the fin portion 147 from the distal direction. As shown in FIG. 27, when the external force acts from the distal direction, the distal side ring 149 moves in the proximal direction. As a result, the pitch of the fin portion 147 is reduced, and the inner diameter of the attachment unit 145 is increased. At this time, the dimension from the longitudinal axis C to the outer peripheral end of the fin portion 147 is D7, and it is greater than dimension D5 in the state that the external force does not act in the directions parallel to the longitudinal axis C. Additionally, the dimension of the attachment unit 145 in the directions parallel to the longitudinal axis C is smaller than that in the state that the external force does not act in the directions parallel to the longitudinal axis C. As described above, the dimension (D3 to D5) from the longitudinal axis C to the outer peripheral end of the fin portion 27 varies in accordance with an acting state of the external force in the directions parallel to the longitudinal axis C.

A function of the endoscope 1 according to this embodiment will now be described. When the insertion section 2 is inserted into the lumen, since the external force acts from the distal direction, the distal side ring 149 moves in the proximal direction. As a result, the dimension from the longitudinal axis C to the outer peripheral end of the fin portion 147 becomes D7, and it is greater than dimension D5 in the state that the external force is not exerted in the directions parallel to the longitudinal axis C. As a result, the fin portion 147 is apt to come into contact with the paries in the large intestine or the small intestine. Therefore, when the attachment unit 25 rotates, propulsive force acting on the insertion section 2 in the distal direction is increased. Therefore, the insertability of the insertion section 2 is improved in the lumen.

On the other hand, when the insertion section 2 is removed from the lumen, since the external force acts from the proximal direction, the proximal side ring 148 moves in the distal direction. As a result, the dimension from the longitudinal axis C to the outer peripheral end of the fin portion 147 becomes D6, and it is smaller than dimension D5 in the state that the external force does not act in the directions parallel to the longitudinal axis C. Therefore, the insertion section 2 can be readily removed by the force in one of the directions parallel to the longitudinal axis C, which is applied by an operator, without rotating the attachment unit 25.

Therefore, in the thus configured endoscope 1, in addition to the same effects as those in the first embodiment, the following effects can be exerted. That is, in the endoscope 1, when the insertion unit 2 is inserted into the lumen, the external force acts from the distal direction. The distal side ring 149 is moved toward the proximal direction by the external force from the distal direction. As a result, the dimension from the longitudinal axis C to the outer peripheral end of the fin portion 147 becomes D7, and it is greater than dimension D5 in the state that the external force does not act in the directions parallel to the longitudinal axis C. As a result, the fin portion 147 is apt to come into contact with the paries in the large intestine or the small intestine. Accordingly, when the attachment unit 25 is rotated, the propulsive force acting on the insertion section 2 toward the distal direction is increased. Therefore, the insertability of the insertion section 2 in the lumen can be improved.

Additionally, in the endoscope 1, when the insertion section 2 is removed from the lumen, the external force acts from the proximal direction. The proximal side ring 148 is moved toward the distal direction by the external force from the proximal direction. As a result, the dimension from the longitudinal axis C to the outer peripheral end of the fin portion 147 becomes D6, and it is smaller than dimension D5 in the state that the external force does not act in the directions parallel to the longitudinal axis C. Therefore, the insertion section 2 can be easily removed by the force in one of the directions parallel to the longitudinal axis C, applied by the operator, without rotating the attachment unit 25.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion main body which is extended along a longitudinal axis, and which is configured to be inserted into a lumen;
   an attachment unit which includes a fin portion spirally extended along the longitudinal axis, and which is provided to an outer peripheral direction side of the insertion main body in a state that a rotation thereof about the longitudinal axis with respect to the insertion main body is controllable, the attachment unit being configured to be unmovable with respect to the insertion main body in directions along the longitudinal axis while the rotation of the attachment unit about the longitudinal axis with respect to the insertion main body is controllable;
   a member inserting portion provided to a proximal direction side of the insertion main body;

an imaging element which is provided inside of the insertion main body, and which is configured to image a subject;
a rotary gear which is attachable to the insertion main body, and which is configured to rotate about a gear axis in a state that the rotary gear is attached to the insertion main body to control the rotation of the attachment unit, that is attached to the insertion main body, about the longitudinal axis;
a partition member which is provided to the proximal direction side of the imaging element in the insertion main body, and which defines a gear arrangement portion on an outer peripheral portion thereof, the rotary gear, that is attached to the insertion main body, being arranged to the gear arrangement portion, the partition member defining the gear arrangement portion in a state that the gear arrangement portion opens toward the outer peripheral direction side at a first opening position and in a state that the gear arrangement portion opens with respect to an inside of the insertion main body at a second opening position, and the partition member being configured to separate the gear arrangement portion from the inside of the insertion main body so that a liquid flowed into the gear arrangement portion does not outflow to the inside of the insertion main body between the first opening position and the second opening position;
a channel tube which is extended inside of the insertion main body, which has one end connected to the member inserting portion, and the other end connected to the partition member at the second opening position, the channel tube being fixed with respect to the insertion main body, a channel which communicates with the gear arrangement portion at the second opening position being provided in the channel tube, and the channel tube being connected to the partition member and the member inserting portion in a state that the liquid flowed into the channel does not outflow to an outside of the channel tube between the member inserting portion and the gear arrangement portion; and
a first linear member which is insertable into the channel from the member inserting portion and removable from the channel through the member inserting portion, the first linear member being configured to move with respect to the channel tube along the gear axis when the first linear member is inserted into the channel and removed from the channel, and the first linear member being rotatable about the gear axis integral with the rotary gear attached to the insertion main body in a state that the first linear member is inserted into the channel.

2. The endoscope according to claim 1, further comprising a drive member to which a proximal end of the first linear member is connected, and which is configured to rotationally drive to rotate the first linear member.

3. The endoscope according to claim 2, further comprising:
a second linear member which is insertable into the channel from the member inserting portion and removable from the channel through the member inserting portion, the second linear member being rotatable about the gear axis integral with the rotary gear attached to the insertion main body in a state that the second linear member inserted into the channel; and
a manual rotation member to which a proximal end of the second linear member is connected, and which is configured to be manually rotated to rotate the second linear member,
wherein one of the first linear member to which the drive member is connected at the proximal end and the second linear member to which the manual rotation member is connected at the proximal end is selectively inserted into the channel.

4. The endoscope according to claim 3,
wherein
the first linear member includes a first switching connecting portion which connects the first linear member to the rotary gear in the state that the first linear member is inserted into the channel, and
the second linear member includes a second switching connecting portion which connects the second linear member to the rotary gear in the state that the second linear member is inserted into the channel.

5. The endoscope according to claim 4,
wherein the member inserting portion includes:
an attachment portion to which the drive member is attached in a state that the first linear member is connected to the rotary gear, and to which the manual rotation member is attached in a state that the second linear member is connected to the rotary gear; and
an elastic member which is configured to maintain water-tightness between the drive member or the manual ration member and the attachment portion, and configured to avoid inflow of a liquid from an outside through the member inserting portion.

6. The endoscope according to claim 2, wherein the drive member is attachable to/detachable from the first linear member.

7. The endoscope according to claim 6, further comprising a manual rotation member to which the proximal end of the first linear member is connectable, and which is configured to be manually rotated to rotate the first linear member when the first linear member is connected thereto, wherein the first linear member includes a switching connecting portion which selectively connects the proximal end of the first linear member to the drive member or the manual rotation member.

8. The endoscope according to claim 7, wherein the member inserting portion includes: an attachment portion to which the drive member connected with the first linear member or the manual rotation member connected with the first linear member is selectively attached; and an elastic member which is configured to maintain water-tightness between the drive member or the manual rotation member and the attachment portion, and configured to avoid inflow of a liquid from an outside through the member inserting portion.

9. The endoscope according to claim 1,
wherein the distal end of the first linear member is detachably attached to the rotary gear, and the first linear member is configured to rotate about the gear axis in a state that the first linear member is connected with the rotary gear attached to the insertion main body to rotate the rotary gear.

10. The endoscope according to claim 9, further comprising:
a rotor to which the attachment unit is fixed without a gap when the attachment unit is attached to the insertion main body in the state that the rotation of the attachment unit is controllable, and which is configured to rotate about the longitudinal axis integrally with the attachment unit, that is attached in the state that the rotation thereof is controllable, with respect to the insertion main body by rotation of the rotary gear attached to the partition member integral with the first linear member.

11. The endoscope according to claim 9,
wherein the attachment unit includes a gear portion which meshes with the rotary gear attached to the partition member without a gap when the attachment unit is attached to the insertion main body in the state that the rotation of the attachment unit is controllable.

12. The endoscope according to claim 1, wherein the partition member defines a hole by which the rotary gear is rotatably supported, one end of the hole being communicated with the gear arrangement portion, the other end of the hole being liquid-tightly blocked.

* * * * *